(12) United States Patent
Tennagels et al.

(10) Patent No.: US 7,732,151 B2
(45) Date of Patent: Jun. 8, 2010

(54) USE OF IRS-POLYPEPTIDES FOR IDENTIFYING OF PHARMACEUTICALLY ACTIVE COMPOUNDS

(75) Inventors: Norbert Tennagels, Frankfurt (DE); Aimo Kannt, Frankfurt (DE); Harald Thuering, Frankfurt (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 587 days.

(21) Appl. No.: 10/849,424

(22) Filed: May 19, 2004

(65) Prior Publication Data

US 2008/0020399 A1    Jan. 24, 2008

Related U.S. Application Data

(60) Provisional application No. 60/520,111, filed on Nov. 14, 2003.

(30) Foreign Application Priority Data

May 22, 2003    (DE)    ................................. 103 23 081

(51) Int. Cl.
   *G01N 33/53*    (2006.01)
   *G01N 33/543*   (2006.01)
(52) U.S. Cl. ........................ 435/7.21; 435/7.1; 436/501; 436/518
(58) Field of Classification Search ........................ None
   See application file for complete search history.

(56) References Cited

U.S. PATENT DOCUMENTS 5,763,198 A * 6/1998 Hirth et al. .................. 435/7.21

FOREIGN PATENT DOCUMENTS

| WO | WO 95/04136 | * | 9/1995 |
| WO | WO 96/40276 | * | 12/1996 |
| WO | WO 98/09169 | | 3/1998 |
| WO | WO 99/29894 | * | 6/1999 |
| WO | WO 00/75167 | | 12/2000 |

OTHER PUBLICATIONS

Schaefer et al. (Analytical Biochemistry, vol. 261, pp. 100-112, 1998).*
Boge et al., A Nonradioactive Assay for the Insulin Receptor Tyrosine Kinase: Use in Monitoring Receptor Kinase Activity after Activation of Overexpressed Protein Kinase C alpha and High Glucose Treatment, Analytical Biochemistry, (1995), vol. 231, pp. 323-332.
Schaefer et al., Detection of Protein Tyrosine Kinase Activity Using a High-Capacity Streptavidin-Coated Membrane and Optimized Biotinylated Peptide Substrates, Analytical Biochemistry, (1998), vol. 261, pp. 100-112.
Siemeister et al., Recombinant Human Insulin Receptor Substrate-1 Protein, The Journal Of Biological Chemistry, (1995), vol. 270, No. 9, pp: 4870-4874.

Aquirre et al., Phosphorylation of Ser307 in insulin receptor substrate-1 blocks interactions with the insulin receptor and inhibits insulin action, J. Biol. Chem. vol. 275, 2000, pp. 9047-9054.
Araki et al., Alternative pathway of insulin signalling in mice with targeted disruption of the IRS-1 gene, Nature, vol. 372, 1994, pp. 186-190.
Araki at al., Human skeletal muscle insulin receotir substrate-1. Characterization of the cDNA, gene, and chromosomal localization., Diabetes, vol. 42, 1993, pp. 1041-1044.
De Fea et al., Protein kinase C modulation of insulin receptor substrate-1 tyrosine phosphorylation requires serine 612, Biochemistry, vol. 36, 1997, pp. 12939-12947.
Eldar-Finkelman et al., Phosphorylation of insulin receptor substrate 1 by glycogen synthase kinase 3 impairs insulin action, Proc. Natl. Acad. Sci. USA, vol. 94, 1997, pp. 9660-9664.
Freund et al., The P13-kinase serine kinase phosphorylates its p85 subunit in IRS-1 and P13-kinase IRS-1 complexes, Biochem Biophys Res Commun. vol. 206, 1995, pp. 272-278.
Gao et al., Serine phosphorylation of insulin receptor substrate 1 by inhibitor kappa B kinase complex, J. Biol. Chem., vol. 277, 2002, pp. 48115-48121.
Jakobsen et al., 5'-AMP-activated protein kinase phosphorylates IRS-1 on Ser-780 in mouse C2c12 myotubes in response to 5-aminoimidazole-4-carboxamide riboside, J. Biol. Chem., vol. 276, 2001, pp. 46912-46916.
Lavan et al., A novel 160-kDa phosphotyrosine protein in insulin-treated embryonic kidney cells is a new member of the insulin receptor substrate family, J. Biol. Chem., vol. 272, 1997, pp. 21403-21407.
Lavan el al., The 60-kDa phosphotyrosine protein in insulin-treated adipocytes is a new member of the insulin receptor substrate family, J. Biol. Chem., vol. 272, 1997, pp. 11439-11443.
Le Marchand-Brustel, Y., Molecular mechanisms of insulin action in normal and insulin-resistant states, Exp. Clin. Endocrinol. Diabetes, vol. 107, 1999, pp. 126-132.
Mothe et al., Phosphorylation of insulin receptor substrate-1 on multiple serine residues 612, 632, 662 and 731, modulates insulin action, J. Biol. Chem., vol. 271, 1996, pp. 11222-11227.
Paz et al., Phosphorylation of insulin receptor substrate-1 (IRS-1) by protein kinase B positively regulates IRS-1 function, J. Biol. Chem., vol. 274, 1999, pp. 28816-28822.
Schmitz-Peiffer et al., Ceramide generation is sufficient to account for the inhibiton of the insulin-stimulated PKB pathway in C2C12 skeletal muscle cells pretreated with palmitate, Ann. NY Acad. Sci. vol. 967, 2002, pp. 146-157.
Sun et al., Structure of the insulin receptor substrate IRS-1 defines a unique signal transduction protein, Nature, vol. 352, 1991, pp. 73-77.
Tanasijevic at al., Phosphorylation of the insulin recetpro substrate IRS-1 by casein kinase II, J. Biol. Chem., vol. 268, 1993, pp. 18157-18166.
Thirone at al., Growth hormone stimulates the tyrosine kinase activity of JAK2 and induces tyrosine phosphorylation of insulin receptor substrates and Shc in rat tissues, Endocrinology, vol. 140, 1999, pp. 55-62.
White, M.F., IRS proteins and the common path to diabetes, Am. J Physiol. Endocrinol. Metabl. vol. 283, 2002, pp. E413-422.

* cited by examiner

*Primary Examiner*—Lisa V Cook

(57) ABSTRACT

An assay for determining the ability of an enzyme, functional fragment, or functional derivative thereof to modify the phosphorylation status of a biotinylated polypeptide.

15 Claims, 12 Drawing Sheets

Figure 1

IRS-1

```
   1 masppesdgf sdvrkvgylr kpksmhkrff vlraaseagg parleyyeme kkwrhkssap
  61 krsiplescf ninkradskn khlvalytrd ehfaiaadse aeqdswyqal lqlhnrakgh
 121 hdgaaalgag ggggscsgss glgeagedls ygdvppgpaf kevwqvilkp kglgqtknli
 181 giyrlcltsk tisfvklnse aaavvlqlmn irrcghsenf ffievgrsav tgpgefwmqv
 241 ddsvvaqnmh etileamram sdefrprsks qsssncsnpi svplrrhhln npppsqvglt
 301 rrsrtesita tspasmvggk pgsfrvrass dgegtmsrpa svdgspvsps tnrthahrhr
 361 gsarlhppln hsrsipmpas rcspsatspv slsssstsgh gstsdclfpr rssasvsgsp
 421 sdggfissde ygsspcdfrs sfrsvtpdsl ghtppargee elsnyicmgg kgpstltapn
 481 ghyilsrggn ghrctpgtgl gtspalagde aasaadldnr frkrthsagt sptithqktp
 541 sqssvasiee ytemmpaypp gggsggrlpg hrhsafvptr sypeeglemh plerrgghhr
 601 pdsstlhtdd gympmspgva pvpsgrkgsq dympmspksv sapqqilnpi rrhpqrvdpn
 661 gymmmspsgg cspdigggps sssssssnavp sgtsygklwt ngvgghhshv lphpkppves
 721 sggkllpctg dymmmspvgd sntsspsdcy ygpedpqhkp vlsyyslprs fkhtqrpgep
 781 eegarhqhlr lstssgrlly aataddssss tssdslgggy cgarlepslp hphhqvlqph
 841 lprkvdtaaq tnsrlarptr lslgdpkast lprareqqqq qqpllhppep kspgeyvnie
 901 fgsdqsgyls gpvafhssps vrcpsqlqpa preeetgtee ymkmdlgpgr raawqestgv
 961 emgrlgpapp gaasicrptr avpssrgdym tmqmscprqs yvdtspaapv syadmrtgia
1021 aeevslprat maaassssaa sasptgpqga aelaahssll ggpqgpggms aftrvnlspn
1081 rnqsakvira dpqgcrrrhs setfsstpsa trvgntvpfg agaavggggg sssssedvkr
1141 hssasfenvw lrpgelggap kepaklcgaa gglenglnyi dldlvkdfkq cpqectpepq
1201 pppppphqp lgsgessstr rssedlsaya sisfqkqped rq
```

(SEQ ID No.1)

IRS-2

```
   1 maspprhgpp gpasgdgpnl nnnnnnnhs vrkcgylrkq khghkrffvl rgpgaggdka
  61 tagggsapqp prleyyesek nwrskagapk rvlaldccln inkradpkhk ylialytkde
 121 yfavaaeneq eqegwyralt dlvsegraaa gdappaaapa ascsaslpga vggsagaaga
 181 edsyglvapa taayrevwqv nlkpkglgqs knltgvyrlc lsartigfvk lnceqpsvtl
 241 qlmnirrcgh sdsffffievg rsavtgpgel wmqaddsvva qnihetilea mkalkelfef
 301 rprsksqssg ssathpisvp garrhhhlvn lppsqtglvr rsrtdslaat ppaakcsscr
 361 vrtasegdgg aaagaaaaga rpvsvagspl spgpvrapls rshtligger aagtkwhcfp
 421 agggglqhsrs msmpvehlpp aatspgslss ssdhgwgsyp pppgphpllp hplhhgpgqr
 481 pssgsasasg spsdpgfmsl deygsspgdl rafcshrsnt pesiaetppa rdggggefy
 541 gymtmndrpls hcgrsyrrvs gdaaqdldrg lrkrtysltt parqrpvpqp ssasldeytl
 601 mratfsqsag rlcpscpass pkvayhpype dygdleigsh rsssssnlgad dgympmtpga
 661 alagsgsgsc rsddympmsp asvsapkqil qpraaaaaaa avpfagpagp aptfaagrtf
 721 pasgggykas spaesspeds gymrmwcgsk lsmehadgkl lpngdylnvs psdavttgtp
 781 pdffsaalhp ggeplrgvpg ccysslprsy kapytcggds dqyvlmsspv grileeenle
 841 pqatpgptqa asafgagptq pphpvvpspv rpsggrpegf lgqrgravrp trlsleglps
 901 lpsmheyplp pepkspgeyi nidfgepgar lsppappla saasssslls asspalslgs
 961 gtpgtssdsr qrsplsdymn ldfsspkspk pgapsghpvg sldgllspea sspypplppr
1021 psaspsssslq pppppppapge lyrlppasav ataqgpgaas slssedtgdng dytemafgva
1081 atppqpiaap pkpeaarvas ptsgvkrlsl meqvsqveaf lqasqppdph rgakviradp
1141 qggrrrhsse tfsstttvtp vspsfahnpk rhnsasvenv slrksseggv gvgpgggdep
1201 ptsprqlqpa pplapqgrpw tpgqpgglvg cpgsggspmr retsagfqng lkyiaidvre
1261 epglppqpqp ppplpqpgd ksswgrtrsl gglisavgvg strggcggpg pgapapcptt
1321 yaqh
```

(SEQ ID No.2)

Figure 1 (Continued)

IRS-3

```
  1 mkpagtgptv ssggestdvs lgppfpwpcp pdvrlcghlr kqksqrrrff vlradpprle
 61 cyesekkfla sgcrpprprr tvslegactl skradarqrh liviytsdss lgvaaaseae
121 qqtwysalle vrataaaaaa tamgfspqea peswifapfq dvwpvtlrsk glgrapglss
181 gsyrlclgsg alsllrkpgs kgsrdsratp ppvlrlslls vrrcghadsf fflelgrsap
241 igpgelwlqa pdavvaqsih etvlaamkrl gssaasgkae aplgdspkga savpapapye
301 lpalalaaqa rspgerakqd yvnplermgs apsyrgpdlg gdyiamgmrn dyvhmggkaa
361 eymwmappgl ppptpprvdp rkepedcest eympmnrflp gplyyefkar epehghssaq
421 csirdrwrpm vaqprssqgs elsgdymyip dypsarlgsl dsclnyvdld lvpplevpga
481 apgnsphsya sikf
```

(SEQ ID No.3)

IRS-4

```
   1 mascsftrdq atrrlrgaaa aaaaalaavv ttpllssgtp taligtgssc pgamwlstat
  61 gsrsdsesee edlpvgeevc krgylrkqkh ghrryfvlkl etadaparle yyenarkfrh
 121 svraaaaaaa aaasgaaipp lippprrvitl yqcfsvsqra daryrhlial ftqdeyfamv
 181 aeneseqesw yllsrlile skrrrcgtlg aqpdgepaal aaaaaaeppf ykdvwqvivk
 241 prglghrkel sgvfrlcltd eevvfvrlnt evasvvvqll sirrcghseq yfflevgrst
 301 vigpgelwmq vddcvvaqnm helflekmra lcadeyrarc rsysisigah lltllsarrh
 361 lglvplepgg wlrrsrfeqf chlraigdge demlfcrrfv tpsepvahsr rgrlhlprgr
 421 rsrravsvpa sffrrlapsp arprhpaeap nngarlssev sgsgsgnfge egnpqgkedq
 481 egsggdympm nnwgsgngrg sgggqgsngq gssshssggn qcsgegqgsr ggqgsngqgs
 541 ggnqcsrdgq gtagghgsgg gqrpgghgs gggqgpgdgh gsgggknsgg gkgsgsgkgs
 601 dgdgergksl kkrsyfgklt qskqqmppp ppppppppa ggtggkgksg grfrlyfcvd
 661 rgatkeckea kevkdaeipe gaargphrar afdededdpy vpmrpgvatp lvsssdympm
 721 apgnvsaskk rhsrspfeds rgymmmfprv spppapsppk apdtnkedds kdndsesdym
 781 fmapgagaip knprnpqggs sskswssyfs lpnpfrsspl gqndnseyvp mlpgkflgrg
 841 ldkevsynwd pkdaaskpsg egsfskpgdg gspskpsdhe ppknkakrpn rlsfitkgyk
 901 ikpkpqkpth eqreadsssd yvnmdftkre sntpapstqg lpdswgilae prqsafsnyv
 961 nvefgvpfpn pandlsdllr alpranplsl dsarwplppl plsatgsnai eeegdyievi
1021 fnsamtpama ladsairyda etgriyvvdp fseccmdisl spsrcseppp varllqeeeq
1081 errrpqsrsq sffaaaraav safptdsler dlspssapav asaaaeptlal sqvvaaasal
1141 aaapgigaaa aaagfdsasa rwfqpvanaa daeavrgaqd vaggsnpgah npsanlargd
1201 nqaggaaaaa aapeppprsr rvprppered sdndddthvr mdfarrdnqf dspkrgr
```

(SEQ ID No.4)

Figure 2

IRS-1

```
   1 cggcggcgcg gtcggagggg gccggcgcgc agagccagac gccgccgctt gttttggttg
  61 gggctctcgg caactctccg aggaggagga ggaggaggga ggagggggaga agtaactgca
 121 gcggcagcgc cctcccgagg aacaggcgtc ttccccgaac ccttcccaaa cctccccat
 181 ccctctcgc ccttgtcccc tcccctcctc cccagccgcc tggagcgagg ggcagggatg
 241 agtctgtccc tccggccggt cccagctgc agtggctgcc cggtatcgtt tcgcatggaa
 301 aagccacttt ctccacccgc cgagatgggc ccggatgggg ctgcagagga cgccgccgcg
 361 ggcggcggca gcagcagcag cagcagcagc agcaacagca acagccgcag cgccgcggtc
 421 tctgcgactg agctggtatt tgggcggctg gtggcggctg ggacggttgg ggggtgggag
 481 gaggcgaagg aggagggaga accccgtgca acgttgggac ttggcaaccc gcctcccct
 541 gccaaggat atttaatttg cctcgggaat cgctgcttcc agaggggaac tcaggaggga
 601 aggcgcgcg gcgcgcgcgc tcctgagggg gcaccgcagg gaccccgac tgtcgcctcc
 661 ctgtgccgga ctccagccgg ggcgacgaga gatgcatctt cgctccttcc tggtgccggc
 721 ggcggctgag aggagacttg gctctcggag gatcggggct gccctcaccc cggacgcact
 781 gcctcccgc cggcgtgaag cgcccgaaaa ctccggtcgg gctctctcct gggctcagca
 841 gctgcgtcct ccttcagctg ccccctcccg gcgcgggggg cggcgtggat ttcagagtcg
 901 gggtttctgc tgcctccagc cctgtttgca tgtgccgggc cgggcgagg agcctccgcc
 961 cccacccgg ttgttttctcg gagcctccct ctgctcagcg ttggtggtgg cggtggcagc
1021 atggcgagcc ctccggagag cgatgccttc tcggacgtgc gcaaggtggg ctacctgcgc
1081 aaacccaaga gcatgcacaa acgcttcttc gtactgcgcg cggccagcga ggctgggggc
1141 ccggcgcgcc tcgagtacta cgagaacgag aagaagtggc ggcacaagtc gagcgccccc
1201 aaacgctcga tcccccttga gagctgcttc aacatcaaca gcgggctga ctccaagaac
1261 aagcacctgg tggctctcta cacccgggac gagcactttg ccatcgcgc ggacagcgag
1321 gccgagcaag acagctggta ccaggctctc ctacagctgc acaaccgtgc taagggccac
1381 cacgacggag ctgcggccct cggggcggga ggtggtgggg gcagctgcag cggcagctcc
1441 ggccttggtg aggctgggga ggacttgagc tacggtgacg tgcccccagg acccgcattc
1501 aaagaggtct ggcaagtgat cctgaagccc aagggctgg gtcagacaaa gaactgatt
1561 ggtatctacc gccttgcct gaccagcaag accatcagct tcgtgaagct gaactcggag
1621 gcagcggccg tggtgctgca gctgatgaac atcaggcgct gtggccactc ggaaaacttc
1681 ttcttcatcg aggtgggccg ttctgccgtg acggggcccg gggagttctg gatgcaggtg
1741 gatgactctg tggtggccca gaacatgcac gagaccatcc tggaggccat gcgggccatg
1801 agtgatgagt tccgccctcg cagcaagagc cagtcctcgt ccaactgctc taacccatc
1861 agcgtccccc tgcgccggca ccatctcaac aatcccccgc ccagccaggt ggggctgacc
1921 cgccgatcac gcactgagag catcaccgcc acctcccggg ccagcatggt ggggcggaag
1981 ccaggctcct tccgtgtccg cgcctccagt gacggcgaag gaccatgtc ccgccagcc
2041 tggtggacg gcagcccgt gagtcccagc accaacagaa cccacgccca ccggcatcgg
2101 ggcagcgcc ggctgcaccc ccgctcaac cacagccgct ccatcccat gccggcttcc
2161 cgctgctgc cttcggccac cagcccacgg agtctgtcgt ccagtagcac cagtggccat
2221 ggctccacct cggattgtct cttcccacgg gcatctagtg cttcggtgtc tggttccccc
2281 agcgatggcc gtttcatctc ctcggatgag tatggctcca gtccctgcga ttccggagt
2341 tccttccgca gtgtcactcc ggattccctg ggccacacc caccagcccg cggtgaggag
2401 gagctaagca actatatctg catggctggc aaggggcccct ccaccctgac cgccccaac
2461 ggtcactaca ttttgtctcg gggtggcaat ggccaccgct gcaccccagg aacaggcttg
2521 ggcacgagtc cagccttggc tggggatgaa gcagccagtg ctgcagatct ggataatcgg
2581 ttccgaaaga gaactcactc ggcaggcaca tccctacca ttaccacca gaagacccg
2641 tcccagtcct cagtggcttc cattgaggag tacacagaga tgatgcctgc ctacccacca
2701 ggaggtggca gtggaggcgg actgcgggga cacaggcact ccgccttcgt gccaccgc
2761 tcctacccag aggagggtct ggaaatgcac ccttggagc gtcgggggggg gcaccaccgc
2821 ccagacagct ccaccctcca cacggatgat ggctacatgc ccatgtcccc aggggtggcc
2881 ccagtgccca gtggccgaaa gggcagtgga gactatatgc ccatgagccc caagagcgta
2941 tctgccccac agcagatcat caatcccatc agacagccatc cccagagagt ggacccaat
3001 ggctacatga tgatgtcccc cagcggtgcc tgctctctg acattggagg tggcccage
3061 agcagcagca gcagcagcaa cgccgtccct tccgggacca gctatggaaa gctgtggaca
3121 aacggggtag gggccacca ctctcatgtc ttgcctcacc ccaaacccc agtggagagc
3181 agcggtggta agctcttacc ttgcacaggt gactacatga acatgtcacc agtgggggac
```

FIGURE 2 (Continued)

```
3241 tccaacacca gcagccctc cgactgctac tacggccctg aggacccca gcacaagcca
3301 gtcctctcct actactcatt gccaagatcc tttaagcaca cccagcgccc cggggagccg
3361 gaggagggtg cccggcatca gcacctccgc ctttccacta gtctggtcg cctcctat
3421 gctgcaacag cagatgattc ttcctcttcc accagcagcg acagcctggg tgggggatac
3481 tgcgggcta ggctggagcc cagccttcca catcccacc atcaggttct gcagcccat
3541 ctgcctcgaa aggtggacac agctgctcag accaatagcc gcctggcccg gccacgagg
3601 ctgtccctgg gggatcccaa ggcagcacc ttacctcggg cccgagagca gcagcagcag
3661 cagcagcct tgctgcaccc tccagagccc aagagcccgg gggaatatgt caatattgaa
3721 tttgggagtg atcagtctgg ctacttgtct ggcccggtgg ctttccacag ctcacttct
3781 gtcaggtgtc catcccagct ccagccagct cccagagagg aagagactgg cactgaggag
3841 tacatgaaga tggacctggg gccgggccgg agggcagcct ggcaggagag cactgggtc
3901 gagatgggca gactgggccc tgcacctccc ggggctgcta gcatttgcag gcctaccgg
3961 gcagtgccca gcagccgggg tgactacatg accatgcaga tgagttgtcc ccgtcagagc
4021 tacgtggaca cctcgccagc tgcccctgta agctatgctg acatgcgaac aggcattgct
4081 gcagaggagg tgagcctgcc cagggccacc atggctgctg cctcctcatc ctcagcagcc
4141 tctgcttccc cgactgggcc tcaggggca gcagagctgg ctgcccactc gtccctgctg
4201 gggggcccac aaggacctgg gggcatgagc gccttcaccc gggtgaacct cagtcctaac
4261 cgcaaccaga gtgccaaagt gatccgtgca gacccacaag ggtgccgcg gaggcatagc
4321 tccgagactt tctcctcaac acccagtgcc acccggtgg gcaacacagt gcctttgga
4381 gcggggcag cagtaggggg cggtggcggt agcagcagca gcagcgagga tgtgaaacgc
4441 cacagctctg cttcctttga gaatgtgtgg ctgaggcctg gggagcttgg gggagcccc
4501 aaggagccag ccaaactgtg tggggctgct gggggtttgg agaatggtct taactacata
4561 gacctggatt tggtcaagga cttcaaacag tgccctcagg agtgcacccc tgaaccgcag
4621 cctccccac ccccaccccc tcatcaaccc ctgggcagcg gtgagagcag ctccaccgc
4681 cgctcaagtg aggatttaag cgcctatgcc agcatcagtt ccagaagca gccagaggac
4741 cgtcagtagc tcaactggac atcacagcag aatgaagacc taaatgacct cagcaaatcc
4801 tctctaact catgggtacc cagactctaa atatttcatg attcacaact aggacctcat
4861 atcttcctca tcagtagatg gtacgatgca tccatttcag tttgtttact ttatccaatc
4921 ctcaggattt cattgactga actgcacgtt ctatattgtg ccaagcgaaa aaaaaaaatg
4981 cactgtgaca ccagaataat gagtctgcat aaacttcatc ttcaacctta aggacttagc
5041 tgccacagt gagctgatgt gccaccctcc gtgtcatgag agaatgggtt tactctcaat
5101 gcattttcaa gatacactc atctgctgct gaaactgtgt acgacaaagc atcattgtaa
5161 attatttcat acaaaactgt tcacgttggg tggagagagt attaaatatt taacataggt
5221 tttgatttat atgtgtaatt ttttaaatga aaatgtaact tttcttacag cacatctttt
5281 ttttggatgt gggatggagg tatacaatgt tctgttgtaa agagtggagc aaatgcttaa
5341 aacaaggctt aaaagagtag aatagggtat gatccttgtt ttaagattgt aattcagaaa
5401 acataatata agaatcatag tgccatagat ggttctcaat tgtatagtta tatttgctga
5461 tactatctct tgtcatataa acctgatgtt gagctgagtt ccttataaga attaatctta
5521 attttgtatt tttcctgta agacaatagg ccatgttaat taaactgaag aaggatatat
5581 ttggctgggt gttttcaaat gtcagcttaa aattggtaat tgaatggaag caaaattata
5641 agaagaggaa attaaagtct tccattgcat gtattgtaaa cagaaggaga tgggtgattc
5701 cttcaattca aagctctct ttggaatgaa caatgtgggc gtttgtaaat tctggaaatg
5761 tctttctatt cataataaac tagatactgt tgatctttta aaaaaaaaa aaaaaaaaa
5821 aaaaaaaa
```

(SEQ ID No.5)

IRS-2:

```
  1 atggcgagcc cgcgcgggca cgggccgccc gggccggcga gggagacgg ccccaacctc
 61 aacaacaaca caacaacaa caaccacagc gtgcgcaagt gcggctacct gcgcaagcag
121 aagcatgcc acaagcgctt cttcgtgctg cgcggacccg gcgcgggcg cgacaaggcc
181 acgcgggcg gggggtcggc gccgcaaccg ccgcggctcg agtactacga aagcgaaaaa
241 aattggcgga gcaaggcagg cgcgccgaaa cgggtgatcg ctctcgactg ctgcctgaac
301 atcaacaagc gcgccgaccc caagcacaag tacctgatcg ccctctacac caaggacgag
361 tacttcgccg tggccgccga gaacgagcag gagcaggagg gctggtaccg cgcgctcacc
421 gacctggtca gcgagggccg cgcggccgcc ggagacgcgc cccgcgcg cgcggccgcc
```

FIGURE 2 (Continued)

```
 481 gcgtcctgca gcgcctccct gccaggcgcc gtgggcggtt ctgccggcgc cgccggggcc
 541 gaggacagct acgggctggt ggctcccgcc acggccgcct accgtgaggt gtggcaggtg
 601 aacctgaagc ccaagggtct gggccagagc aagaacctga cggggtgta ccgtctgtgc
 661 ctgtctgcgc gcaccatcgg cttcgtgaag ctcaactgcg agcagccgtc ggtgacgctg
 721 cagctcatga acatccgccg ctgcggccac tcggacagct tcttcttcat cgaggtgggc
 781 cgctcggccg tcacaggccc cggcgagctg tggatgcagg cggacgactc ggtggtgggcg
 841 cagaacatcc acgagaccat cctggaggcc atgaaggcgc tcaaggagct cttcgagttc
 901 cggccgcgca gtaagagcca atcgtcgggg tcgtcggcca cgcacccat cagcgtcccc
 961 ggcgcgcgcc gccaccacca cctggtcaac ctgccccca gccagacggg cctggtgcgc
1021 cgctcgcgca ccgacagcct ggccgccacc ccgccggcgg ccaagtgcag ctcgtgccgg
1081 gtgcgcaccg ccagcgaggg cgacggcggc gcggcggcgg gagcggcggc cgcgggcgcc
1141 aggccggtgt cggtggctgg gagccccctg agccccggc cggtgcgcgc gcccctgagc
1201 cgctcgcaca ccctgatcgg cggctgccgg gccgcgggaa caaagtggca ttgcttccg
1261 gcaggggcg gattgcaaca cagccgttcg atgtccatgc ccgtggagca tttgccgcca
1321 gccgccacca gccgggttc cttgtcttcc agcagcgacc acggttgggg ttcttacccg
1381 ccgccgccg gccgcaccc gcttttgccg catccgttgc accacggcc cggccagcgg
1441 ccttccagcg gcagcgcttc cgcttcgggc tccccagcg accccggttt catgtccctg
1501 gacgagtacg gctccagccc aggcgacctg cgcgccttct gcagccaccg aagcaacacg
1561 cccgagtcca tgcggagac gccccggcc cgagacgggc gcgggccgg tgagtttac
1621 gggtacatga ccatgacag gccctgagc cactgtggcc gctcctaccg ccgggtctcg
1681 ggggacgcgg cccaggacct ggaccgaggg ctgcgcaaga ggacctactc cctgaccacg
1741 ccagcccggc agcggccggt gccccagccc tcctctgcct cgctggatga atacaccctg
1801 atgcgggcca cctctcgggg cagcgcggc cgcctctgcc cgtcctgccc cgcgtcctct
1861 cccaaggtgg cctaccaccc ctacccagag gactacggag acatcgagat cggctcccac
1921 aggagctcca gcagcaacct gggggcagac gacggctaca tgcccatgac gccggcgcg
1981 gccttgcgg gcagtgggag cggcagctgc aggagcgacg actacatgcc catgagcccc
2041 gccagcgtgt ccgccccaa gcagattttg cagcccaggg ccgccgccgc cgccgcgcc
2101 gccgtgcctt ttgcggggcc tgcggggcca gcacccacct ttgcggcggg caggacattc
2151 ccggcgagtg ggggcggcta caaggccagc tgcccgccg agagctcccc cgaggacagt
2221 gggtacatgc gcatgtggtg cggttccaag ctgtccatgg agcatgcaga tggcaagctg
2281 ctgccaacg gggactacct caacgtgtcc cccagcacg cggtcaccac gggcacctgc
2341 ccgacttct tctccgcagc cctgcacccc ggcggggagc cgctcagggg cgttccggc
2401 tgctgctaca gctccttgcc ccgctcctac aaggcccct acacctgtgg cggggacagc
2461 gaccagtacg tgctcatgag ctcccccgtg gggcgcatcc tggaggagga gcgtctggag
2521 cctcaggcca ccccagggcc cacccaggcg gccagcgcct tggggccgg cccacgcag
2581 cccctcacc ctgtagtgcc ttcgccgtg cggcctagcg gcggccgcc ggagggcttc
2641 ttgggccagc gcggccgggc ggtgaggccc acgcgcctgt cctggagggg gctgccagc
2701 ctgccagca tgcacgagta cccactgcca ccggagccca agagcccgg cgagtacatc
2761 aacatcgact ttggcgagcc cggggccgc ctgtcgccgc ccgcgcctcc cctgctggcg
2821 tcggcggcct cgtcctcatc gctattgtcc gccagcagcc cggccttgtc gttgggctca
2881 ggcacccgg gcaccagcag cgacagccgg cagcggtctc cgctctccga ctacatgaac
2941 ctcgacttca gctccccaa gtctcctaag ccgggcgcc cgagcggcca ccccgtgggc
3001 tccttggacg gcctcctgtc cccggaggcc tcctcccgt atccgcgtt gccccgcgt
3061 ccgtccgcgt cccgtcgtc gtctctgcag ccgcgccac cgccgcgcc ccggggggag
3121 ctgtaccgcc tgccccggc ctcgcgcgtt gccaccgccc agggcccggg cgccgcctca
3181 tcgttgtcct cggacaccgg ggacaatggt gactacaccg agatggcttt tggtgtggcc
3241 gccacccgc cgcaacctat cgcggcccc ccgaagccag aagctgcccg cgtggccagc
3301 ccgacgtcgg gcgtgaagag gctgagcctc atggagcagg tgtcgggagt cgaggccttc
3361 ctgcaggcca gccagcccc ggaccccac cgcggcgcca aggtcatccg cgcagaccg
3421 cagggggcc gccgccgcca cagttccgag accttctcct ccaccacgac ggtcacccc
3481 gtgtcccgt ccttcgccca caacccaag cgccacaact cggcctccgt ggaaaatgtc
3541 tctctcagga aaagcagcga gggcggcgtg ggtgtcggcc ctggaggggg cgacgagccg
3601 cccacctccc cacgacagtt gcagccggcg ccccctttgg caccgcaggg ccggccgtgg
3661 acccggagc agccggggg cttggtcggt tgtcctggga gcggtggatc gcccatgggc
3721 agagagacct ctgccggttt ccagaatggt ctcaagtaca tcgccatcga cgtgagggag
3781 gagccgggc tgccacccca gccgcgaccg ccgccgccgc cgcttcctca gccgggagac
3841 aagagctcct ggggccggac ccgaagcctc ggggtctca tcagctctgt ggggtcggc
3901 agcacccgcg gcgggtgcgg ggggccgggt ccggtgccc ctgccctg cccaacaacc
3961 tacgcccagc attga
```

FIGURE 2 (Continued)

(SEQ ID No. 6)

IRS-3

```
   1 gggacacacg cacectgtac aggctccttg cccactccaa gtcaggagag ggcgtggaga
  61 gatgcagggc agctaggccg gttgcaatct tcccaagatt gcaacttgtc ccaagccggt
 121 ggtagctcag gggacaggac ccattcaaat tagtccttct gaggacagtt tactgccttt
 181 ggctggagat gaagcctgca ggtacgggcc ccacagtctc ctctggggge gagtccaccg
 241 acgtgtccct cggcccgccg tttccttggc cctgcccgcc cgacgtgcgg ctctgtggcc
 301 atctgaggaa gcagaagtcc cagcgccgcc gcttttcgt gctgcgtgct gacccaccac
 361 ggctggagtg ctatgagagc gagaagaagt tcttggccag cggctgccgc ccacctcgac
 421 cccggcgtac cgttagcctg gaaggtgcct gcactattag caagcgcgcg gatgcccgtc
 481 agcgccacct gatcgtcatc tataccagcg acagcagcct gggcgtggcc gcgccagtg
 541 aagcagagca gcaaacatgg tacagcgcct tgctcgaggt gcgcgccacc gccgctgcag
 601 ctgccgcac cgctatgggt ttcagcccc aagaggcccc tgagtcttgg atcttcgccg
 661 cgttccagga cgtctggcct gtgacactgc ggtccaaggg gctggggaga gcaccaggcc
 721 tgagcagcgg cagctatcgc ctgtgcctgg gttctggggc cctgagcctc ctgcggaagc
 781 cgggaagcaa aggctccaga gacagccggg caacgccacc accagtcctg cgcttgtcct
 841 tgcttagtgt gcgccgctgc ggccacgcag attccttttt cttctggaa ctcgggcgct
 901 cagcgcccat aggtcctggt gagctgtggc tgcaggcccc tgatgcagtg gtggcccaaa
 961 gcattcatga daccgtcctg gctgccatga agagactggg gagcagtgca gccagtggca
1021 aagctgaggc accgctggga gattctccaa aggggcttc tgcagtcct gcccagcac
1081 catatgagat ccctgctttg gcactggcag cacaagcgag aagtccgggt gagagagcga
1141 agcaggacta cgtcaatcca ctggaaagga tggggtcagc accctcctac aggggccag
1201 atctgggtgg ggactacatc gccatgggaa tgaggaatga ctatgtgcac atggggggga
1261 aagctgctga gtacatgtgg atggcgcccc caggtctccc tcccccacc cctccaggg
1321 tagatcccag aaaggagcct gaggattgtg agagcacaga gtatatgccc atgaacagat
1381 ttttaccggg gcctctttac tacgagttca aggccaggga gctgaacat gggcattcta
1441 gtgcccagtg tagcattagg gacagatgga gacccatggt ggctcagccc cgctcttccc
1501 aagggtcaga gctctctggg gactacatgt acatccctga ctatcccagt gctaggctgg
1561 ggtctctgga cagctgcctc aactatgtgg acctggacct agtccctccc ctggaggttc
1621 ctggagcggc cccagggaat agtccacata gctatgccag catcaagttc tagaactttc
1681 agaagatagg ggaggagaac caagcattgg ttagggaaga gaggaaaaga agagaaaacc
1741 ttagcactgt tcagctcagc ttctgcacat aggagccagg gactctgagg ccttgtgagg
1801 tgctatgctg cccccttgcc tgctctgtct cttccagctg tacggcctca gaaacacctc
1861 aggaagaagt gctccaaaga aattagactc ttaagagaaa gtactagaac atctctctgc
1921 accccaccc caaacccaaa caacaaacaa ataaaacacc tacagaacc
```

(SEQ ID No.7)

IRS-4

```
   1 ggtcagggta gttccccaac cctcccttc gtgaattccc cctcgtcctc gctcacctta
  61 aaaccatcgt gcatcaccat ggcgagttgc tccttcactc gcgaccaagc gacaagaaga
 121 ctaagaggtg cagcagcggg ggcagcggca gctctagcag cagtggtgac caccccgctt
 181 ctttcctcgg gaaccccgac cgcactcatt gggacgggt cgtcttgtcc gggagccatg
 241 tggctctcca cggccactgg ctccggtca gactccgagt ccgaagagga ggacctgccc
 301 gtcggggagg aagtctgcaa acgcggctac ctgcggaaac agaagcatgg gcacaggcgc
 361 tacttcgtgc tcaaactcga gactgctgac gccccagctc ggctggaata ctacgaaaat
 421 gccaggaagt tccggcacag tgtccgcgcc gcggcggctg cagcagcggc ggcgcctct
 481 ggcgccgcga tccccccgct cattccaccg cggcgcgtga taccctata ccagtgcttt
 541 tccgtgagcc agcgagcaga tgcaaggtac cgacacctca ttgctctttt cacccaagac
 601 gaatacttcg cgatggtggc gcgagaacgag tccaggcagg aaagctggta cttgctgctc
 661 agccgcctca tcctcgagag caagagccca cgctgggca cgtcgcgcg gcagccggac
 721 ggagagccgg ccgcgctggc ggcggcagcg gcgcggagc caccccttcta taagatgtg
```

FIGURE 2 (Continued)

```
 781 tggcaggtaa tagtcaaacc caggggggctg gggcacagaa aagagctgag cggcgtgttc
 841 cggctgtgtc taaccgacga ggaggtcgtg tttgtgaggc tgaacaccga agtggccagc
 901 gtggtcgtcc agctcctgag catccgtcgc tgtggacact cggagcagta tttcttcttg
 961 gaagtaggca ggtccactgt catcggtccg ggagagctct ggatgcaggt cgatgactgt
1021 gtggttgccc aaaacatgca tgagctgttt ttggagaaga tgagagcctt gtgtgcagac
1081 gaatacagag cccgctgccg cagctacagc atcagcatcg gcgcccacct gttaaccctg
1141 ctgtccgcta ggaggcacct gggcttggtg ccgctcgagc cgggaggctg gctcagaagg
1201 tcccgctttg agcagttttg ccacctcagg gccatcggcg acggggaaga cgagatgctt
1261 ttcaccaggc gcttcgtaac cccagcgag cctgtggccc actccaggcg aggaagactg
1321 cacctgccca gagggcgcag gtcaaggaga gcggtttcag tgccggccag cttttttcgc
1381 cgcttagcac ccagcccagc acgtccccgg caccctgcag aagccccgaa caatggagct
1441 cgctgtgtct ctgaagtgtc tggttctggc tctggcaact tggggagga aggcaatccc
1501 cagggcaaag aagatcagga aggaagcgga ggtgactaca tgcctatgaa caattggggc
1561 tcaggaaatg gccgggggctc aggaggtggc cagggctcaa atggccaagg ctccagtagc
1621 catagctcgg gaggaaacca gtgttcaggc gagggacagg gatcccgagg tggtcagggc
1681 tcaaatggcc agggctcagg aggaaaccag tgctctagag atggccaggg caccgcaggt
1741 gggcacggtt caggtggtgg ccagagacct ggaggtgggc atggctcagg tggtggccag
1801 ggacctggag atggccatgg ctcaggtggt ggcaagaact ctggggggggg caaaggctca
1861 ggaagtggga aaggatccga tggtgatggt gaacgtggaa aatctctgaa gaaaagatcc
1921 tattttggca aattaactca aagcaagcaa cagcaaatgc caccacctcc accacctcct
1981 cctccacccc caccagctgg aggaactggt ggaaaaggga agtctggggg aagattcaga
2041 ctttattttt gtgttgacag aggagccacg aaagaatgca aagaagccaa agaagtgaaa
2101 gatgcagaga tcccagaagg tgcagctcga ggtccccaca gagccagagc ttttgatgaa
2161 gatgaggatg acccatacgt gccaatgagg ccaggggtgg ccaccccctct tgtaagctcc
2221 agtgattata tgccaatggc tcctcaaaat gtctctgctt caaaaaagcg ccactctcga
2281 tccccttttg aagattcaag agggtacatg atgatgtttc ccagagtgag cccaccacct
2341 gctccgagtc ctccaaaagc acctgatact aataaagagg atgactcaaa ggacaatgac
2401 agtgagagtg actacatgtt tatggctcct ggagccggtg caattccaaa aaacccagga
2461 aatcctcagg gtggctcttc ctccaaaagt tggagctcct actttctctct accaaacctt
2521 tttcggagct cacctttggg acagaatgac aacagtgagt atgtgccaat gttacctgga
2581 aagttcctgg ggaggggcct agacaaagaa gtctcctata actgggaccc caaagatgca
2641 gcttcaaagc cttcaggtga gggatcattc tcaaagcctg gagatggggg atcacttca
2701 aagccttcag atcatgagcc cccaaagaat aaagctaaga gacctaaccg actttcttt
2761 attacaaaag gatataaaat caagccaaaa ccacaaaagc ccacacatga gcagagagaa
2821 gctgacagct ctagtgacta cgtcaacatg gacttcacta aagagagag caatacacca
2881 gctccctcta ctcaaggact accagattcg tggggcataa ttgctgaacc cagacagtca
2941 gccttttcta attatgtgaa tgttgagttt ggagtgccat tccaaatcc agcaaacgac
3001 ctctcagatc ttttaagagc tataccacgt gccaacccct tatctctgga cagtgctagg
3061 tggccacttc ctcccttcc cctcagtgct acaggtagca atgctattga ggaagagggt
3121 gactacattg aagtaatttt caactcagca atgacaccag ccatggctct tgctgacagt
3181 gccattcgct atgatgctga aacaggtcga atctatgtgg tgacccatt ttctgagtgc
3241 tgtatggata tttctctctc cccagccga tgttctgaac caccctgt agctaggctg
3301 ctgcaggaag aagagcagga gagaagacgc ccacaaagcc gttctcaaag tttcttgca
3361 gcagccagag ccgctgtctc tgcttttcca acagacagcc tgagagaga cctttcccca
3421 tcctcagccc cggctgtcgc ttcggctgca gagccgactt tagccctcag ccaagttgta
3481 gctgcggcct ccgcgctcgc cgcagcccg ggcatcggcg cagcagccgc agctgctgga
3541 tttgactccg cctctgcccg ctggtttcaa cctgttgcta atgctgctga tgccgaagca
3601 gtaaggggag cccaagacgt tgccggtggc tcgaaccctg gagcccacaa cccatctgca
3661 aaccttgcca gaggtgataa ccaggctggc gggctgccg ctgcagctgc cgctcggaa
3721 ccaccacctc gcagtcgccg ggtgccaaga ccccggaga gagaagattc tgacaacgac
3781 gacgacactc acgtgagaat ggattttgcc agacgtgata atcagttcga ctctcccaaa
3841 agaggtcggt aattttagaa ttaatttccc taaagtgaat ggtcattgtc taatgattcg
3901 atgcgctaca gtctacagtg ttagggtata tttcattaa
```

(SEQ ID No.8)

Figure 3

Amino acid sequence of the 262 AA-long IRS-1 fragment (SEQ ID No. 9).

```
516 -DLDNR  FRKRTHSAGT  SPTITHQKTP
    SQSSVASIEE  YTEMMPAYPP  GGGSGGRLPG
    HRHSAFVPTR  SYPEEGLEMH  PLERRGGHHR
    PDSSTLHTDD  GYMPMSPGVA  PVPSGRKGSG
    DYMPMSPKSV  SAPQQIINPI  RRHPQRVDPN
    GYMMMSPSGG  CSPDIGGGPS  SSSSSSNAVP
    SGTSYGKLWT  NGVGGHHSHV  LPHPKPPVES
    SGGKLLPCTG  DYMNMSPVGD  SNTSSPSDCY
    YGPEDPQHKP  VLSYYSLPRS  FKHTQRP-777
```

USE OF IRS-POLYPEPTIDES FOR IDENTIFYING OF PHARMACEUTICALLY ACTIVE COMPOUNDS

RELATED APPLICATIONS

This application claims the benefit of priority under 35 U.S.C. § 119 of German Application No. 103 23 081.5 filed May 22, 2003, and of U.S. Provisional Application No. 60/520,111 filed Nov. 14, 2003, the contents of both of which are incorporated by reference.

BACKGROUND

This invention relates to the use of a polypeptide for determining the ability of an enzyme to modify the phosphorylation state of the polypeptide. Further aspects of the invention relate to a method for determining such an activity, and to a method for identifying substances which modify this ability of the enzyme.

Insulin is a peptide hormone which influences a large number of growth and metabolic pathways by binding to the insulin receptor and thus activating its intrinsic tyrosine kinase. This event leads to phosphorylation of a large number of proteins able to bind to the insulin receptor (IR), to specific tyrosine residues. The family of insulin receptor substrate (IRS) proteins also belongs to the proteins phosphorylated in this way.

Insulin receptor substrate 1 (IRS-1) is a cellular protein which can be phosphorylated by a large number of protein kinases (tyrosine-specific or serine/threonine-specific protein kinases) on tyrosine and/or serine residues and or threonine residues. It is assumed in this connection that there is specific phosphorylation of different tyrosine or serine/threonine residues depending on the enzyme. Apart from phosphorylation by tyrosine kinases such as, for example, apart from the insulin receptor (White 2002), the IGF-1 receptor (White 2002) or JAK 1/2 (Thirone et al. 1999), it is known that IRS-1 is also phosphorylated by serine/threonine kinases such as, for example, kinases from the PKC family (Schmitz-Peiffer 2002), inhibitor kappa B kinase complex (Gao et al. 2002), c-Jun NH(2)-terminal kinase (JNK, Aguirre et al. 2000) protein kinase A (Sun et al. 1991), mitogen-activated protein kinase (Mothe et al. 1996), protein kinase B (Paz et al. 1999), casein kinase (Tanasijevic et al. 1993), glycogen synthase kinase beta (Eldar-Finkelmann et al. 1997), AMP-activated kinase (Jakobsen et al. 2001) or phosphoinositol 3 kinase (Freund et al. 1995). IRS molecules are key molecules in the insulin signal transduction pathway and play a central role in maintenance of cellular functions such as growth, survival and metabolism. Phosphorylated IRS proteins serve in this connection as "docking" proteins with a large number of docking sites for the insulin receptor and with a complex network of intracellular signal molecules with so-called signal recognition complex (SRC) homology 2 domains (SH2 domains). Activation of these Sh2 domain proteins moreover activates certain signal cascades, which in turn leads to activation of various effectors which are located further downstream in the signal cascade, ultimately leading to transmission of the insulin signal to a branched series of other intracellular signal cascades (for review, see White 2002).

IRS belongs to a group of phosphoproteins which have a size of from 160 to 185 kDA and which serve as substrate of the insulin receptor. Four members of the IRS family (IRS-1, IRS-2, IRS-3 and IRS-4) are known. They differ in tissue distribution, subcellular localization, development-specific expression, nature of binding to the insulin receptor and nature of the SH2 proteins with which they interact. The four members of the IRS family have very similar structures in terms of their underlying protein structure: all have an amino (N)-terminal plextrin homology domain (PH domain) which binds to membrane phospholipids, a phosphotyrosine-binding domain (PTB domain) which is connected directly to the carboxy (C) terminus of the PH domain and is involved in the recognition of the Asp-Pro-Glu phosphotyrosine (NPEpY) sequence which is located in the juxtamembrane region of the insulin receptor beta subunit. They have moreover a somewhat less strongly conserved C-terminal part which has various potential tyrosine phosphorylation motifs to which specific SH2 domain-containing proteins can bind.

IRS-1 comprises 21 possible tyrosine phosphorylation sites, of which some are located in amino acid sequence motifs able to bind to the SH2 domain proteins. IRS-1 additionally comprises 30 potential serine/threonine phosphorylation sites in motifs which can be recognized by various kinases, such as, for example, kinases from the PKC family (Schmitz-Peiffer 2002), inhibitor kappa B kinase complex (Gao et al. 2002), c-Jun NH(2)-terminal kinase (JNK, Aguirre et al. 2000) protein kinase A (Sun et al. 1991), mitogen-activated protein kinase (Mothe et al. 1996), protein kinase B (Paz et al. 1999), casein kinase (Tanasijevic et al. 1993), glycogen synthase kinase beta (Eldar-Finkelmann et al. 1997), AMP-activated kinase (Jakobsen et al. 2001) or phosphoinositol 3 kinase (PI3 kinase, Freund et al. 1995). Inhibitory effects on the insulin receptor signal pathway can be explained at least in part by the recently discovered role of the serine/threonine phosphorylation of IRS-1, which is thought to be connected with an impairment of the interaction with the insulin receptor and/or a reduction in the in the tyrosine phosphorylation of IRS-1 and/or an impairment of the interaction with subsequent signal proteins able to bind to tyrosine-phosphorylated IRS-1 (for review, see White 2002). It has been possible to date to demonstrate for various kinases, for example kinases from the PKC family (Schmitz-Peiffer 2002), inhibitor kappa B kinase complex (Gao et al. 2002), c-Jun NH(2)-terminal kinase (JNK, Aguirre et al. 2000) protein kinase A (Sun et al. 1991), mitogen-activated protein kinase (Mothe et al. 1996), protein kinase B (Paz et al. 1999), casein kinase (Tanasijevic et al. 1993), glycogen synthase kinase beta (Eldar-Finkelmann et al. 1997) or phosphoinositol 3 kinase (Freund et al. 1995), that they phosphorylate IRS-1 directly in vitro. Moreover, in every case, an increased kinase activity in intact cells inhibited the activity of the insulin signal transduction pathway. In addition, the in vitro phosphorylation of RS-1 on serine/threonine residues was in some studies thought to be directly connected to the reduced tyrosine phosphorylation by the insulin receptor (Le Marchand-Brustel 1999)).

The sequences of IRS-1, 2, 3 and 4 are available to the public. The coding polynucleotide sequences and the relevant protein sequences of these genes can be accessed under the numbers NM_005544 (IRS-1 hs), XM_007095 (IRS-2 hs), NM_032074 (IRS-3 rat), NM_003604 (IRS-4 hs) from the NCBI nucleotide database.

NCBI is the National Center for Biotechnology Information (postal address: National Center for Biotechnology Information, National Library of Medicine, Building 38A, Bethesda, Md. 20894, USA; web address: www.ncbi.nhm.nih.gov). Cloning of the IRS-1 gene has been described inter alia in Araki et al. 1993 and Siemeister et. al, 1996; cloning of IRS-2 to 4 has been described by Araki et al 1994, Lavan et al. 1997a and Lavan et al. 1997b.

Various prior art methods are known for determining the ability and for measuring the activity of various kinases to phosphorylate IRS-1, the methods being based either on radioactive detection methods (e.g. transfer of radiolabeled phosphate to the substrate) or nonradioactive detection methods.

Thus, it is known to determine the phosphorylation of IRS-1 on full-length IRS-1 protein, fragments or peptides thereof which still have at least one phosphorylation site by a method in which radioactive phosphate residues are transferred to IRS-1 by incubation with radiolabeled ATP and the kinase to be tested as a function of the ability of the kinase to phosphorylate IRS-1. This is followed by chromatographic or electrophoretic fractionation of the IRS-1 and detection of the amount of transferred phosphate by flow scintillation or autoradiography (as described for example for the complete IRS-1 protein and glycogen synthase kinase 3 beta in Eldar-Finkelman et al. 1997, for a fragment of IRS-1 (amino acid 516-777) and insulin receptor, IGF-1 receptor or recombinant insulin receptor kinase in Siemeister et al. 1995 or an IRS-1 peptide (amino acid 601-616) with cell lysates which contain activated protein kinase from the PKC family in De Fea et al. 1997. In addition, it is from Siemeister et al. 1995 to determine the ability to phosphorylate IRS-1 fragments, for example a fragment of IRS-1 (amino acid 516-777) and insulin receptor, IGF-1 receptor or recombinant insulin receptor kinase by incubation with radiolabeled ATP, dropwise addition of the substrate to a positively charged membrane (nitrocellulose or similar material), washing and detection of the bound radiolabeled substrate by means of autoradiography or measurement of the radioactive emission.

Incubation of a biotinylated IRS-1 peptide (amino acid 601-616) with radiolabeled ATP, dropwise addition of the substrate to a streptavidin-coated membrane, washing and detection of the bound radiolabeled substrate by autoradiography or measurement of the radioactive emission is a further method for determining the ability of kinases to phosphorylate IRS-1 (see De Fea et al. 1997).

The disadvantage of the radioactive assay methods described above is obvious, because handling radioactivity entails considerable risks, is very costly and thus has low suitability in particular for high throughput methods (HTS methods).

The disadvantage of the methods described above which are based on the use of short peptides is that these peptides have unfavorable kinetic constants (Vmax, Km) and moreover the three-dimensional structure of peptides differs greatly from that of the physiological enzyme substrates. This is manifested on the one hand by a completely different folding, so that certain biological spaces which determine the specificity of the enzyme-substrate interaction are not present, which results either in a lack of recognition (and thus modification) or in a nonspecific recognition (and thus modification) and ultimately leads to incorrect results. Moreover, the shortness of peptides means that they have only one or a few phosphorylation sites, so that diverse peptides are necessary to investigate the phosphorylation modification of a particular substrate by different enzymes. This in turn also results in increased costs and an only conditional applicability for methods in the HTS format.

The object of the invention is therefore to provide a possible way of determining the activity of protein-phosphorylating and/or -dephosphorylating enzymes which does not have the abovementioned disadvantages.

This object is achieved by the use of a polypeptide (Def GGs to the peptide) to determine the ability of an enzyme, of a functional fragment or derivative thereof, to modify the phosphorylation status of a polypeptide, wherein the polypeptide is biotinylated.

BRIEF DESCRIPTION OF THE FIGURES

FIG. 1 shows the protein sequences of IRS 1-IRS 4 (SEQ ID No. 1 to 4). The sequence access numbers (NCBI protein database) of the four family members are NM_005544 (IRS-1 hs), XM_07095 (IRS-2 hs), NM_032074 (IRS-3 rat), NM_03604 (IRS-4 hs).

FIG. 2 shows the coding DNA sequences of IRS 1-IRS 4 (SEQ ID No. 5 to 8). The sequence access numbers (NCBI nucleotide database of the four family members are NM_005544 (IRS-1 hs), XM_007095 (IRS-2 hs), NM_032074 (IRS-3 rat), NM_003604 (IRS-4 hs).

FIG. 3 shows the domain of the IRS-1 protein (hIRS-1-p30), comprising 262 amino acids, which was employed for the present studies. Serines 612, 632, 662 and 731 are shown underlined. YXXM tyrosine phosphorylation motifs are shown in bold.

DETAILED DESCRIPTION OF THE INVENTION

Figure 4:
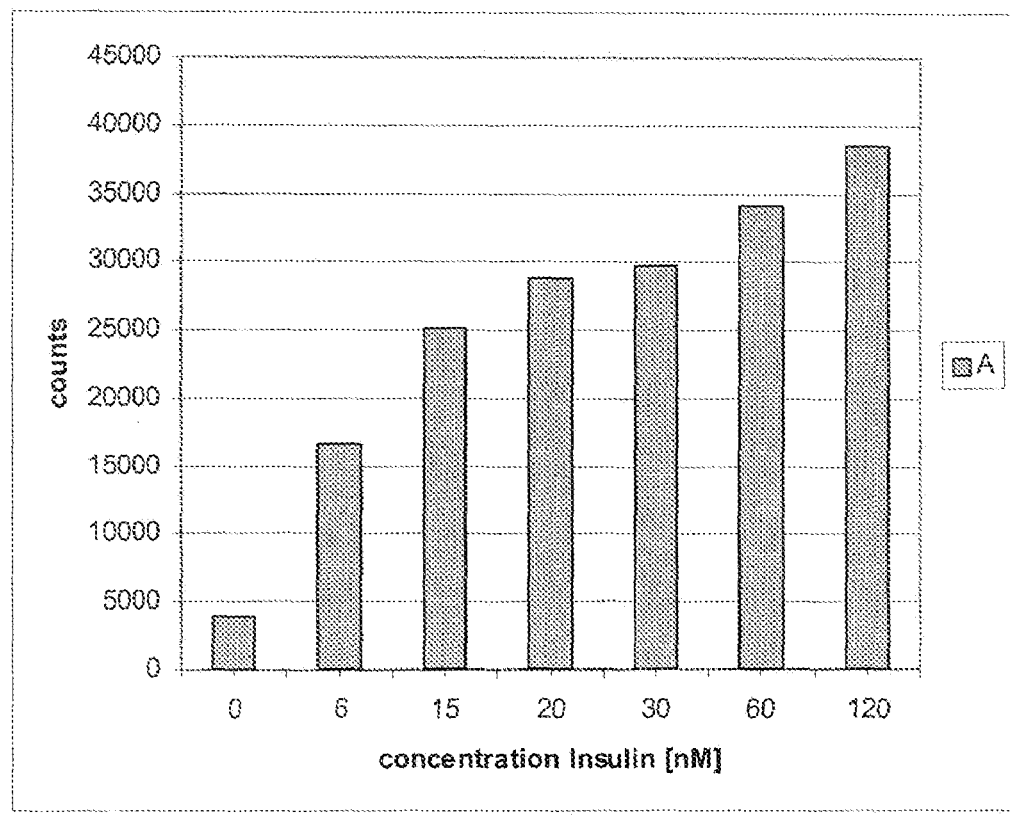
FIGS. 4 and 5 show the results of an ALPHAScreen assay using insulin receptor purified by wheat germ lectin affinity chromatography FIG. 6 summarizes the interactions of insulin receptor, IRS-1, and serine kinases.

The invention is based on the inventors' results which surprisingly showed that even with polypeptides or full-length proteins there was no steric hindrance of the biotin binding by streptavidin, and the biotinylation did not interfere with the phosphorylation of the investigated substrate by kinases either.

The term polypeptide means for the purposes of the present invention a molecule comprising amino acids linked by peptide bonds and having at least 50 amino acids linked linearly in this way. Shorter molecules of this type are referred to as peptides.

The term protein relates to molecules which comprise at least one polypeptide chain but which may also consist of a plurality of polypeptide chains associated or linked together. The term protein thus includes the term polypeptide.

In a preferred embodiment of the various aspects of the present invention, the polypeptide has a length of 50 amino acids and more, preferably 50-300.

In a further preferred embodiment of the various aspects of the invention, the polypeptide has a size of 1 kDa and more, preferably 1 to 100 kDa and particularly preferably 10 to 50 kDa.

A substrate of an enzyme means in the present text any molecule suitable for modification by the enzyme. Natural substrates are for the purposes of the present inventions molecules which are arranged in the way in which they occur in the physiological or pathological context in nature and are able to be modified by the relevant enzyme.

Modulation of the phosphorylation state by the enzyme refers to the nature of the modification of a substrate by an enzyme in which at least one phosphate group is transferred to the substrate or removed. The enzymes relevant to the present invention therefore have the ability to catalyze one and/or the other reaction. They therefore have at least this ability of kinases and/or phosphatases, but may in addition also have further enzymatic properties (e.g. protease properties etc.). The various enzyme categories and their properties are sufficiently well known to the relevant skilled worker.

A functional fragment of an enzyme is in the present text any fragment of the enzyme (i.e. a molecule which is reduced in size or truncated compared with the naturally occurring form) that still has the ability to modify the phosphorylation state of at least one polypeptide. The term "functional derivative" of an enzyme in this connection includes every type of modification of the enzyme compared with the form occurring in nature, which does not represent a truncation, the derivative of the enzyme still having the ability to modify the phosphorylation state of at least one polypeptide. In this connection, the present invention also relates to functional derivatives of fragments of enzymes which are able to modify the phosphorylation state of at least one polypeptide.

Determination of the ability of the enzyme to modify the phosphorylation state of the polypeptide may in this connection take place both qualitatively and quantitatively (i.e. as a quantifiable measurement).

The use according to the invention has the advantage that the results achieved thereby are more informative, owing to the length of the substrates used, because they include a tertiary structure which tends to correspond to physiological circumstances. In addition, the polypeptides used have, by contrast with the peptides known in the prior art, good kinetic constants (e.g. for IRS-1: Km 19 µM: compared with peptides: >200 µM, cf. Siemeister et al. 1995) and only one substrate is necessary for analyzing substrates with a plurality of phosphorylation sites and can be used for example also to determine the ability of different enzymes.

A preferred embodiment relates to a use in which the ability of an enzyme to phosphorylate the polypeptide is determined.

Particularly expedient types of enzymes having kinase activity for the various aspects of the present invention relate to serine/threonine or tyrosine kinases. Particularly suitable examples of kinases include inter alia the insulin receptor, IGF-1 receptor, trK receptor, EGF receptor, casein kinase II, members of the protein kinase C family, protein kinase B/Akt, mitogen-activated protein kinase (MAP kinase), GSK-3 beta, ERK1/2, IKK beta kinase, AMP kinase, PI3 kinase or JNK.

The use according to the invention is additionally equally suitable for determining the ability of an enzyme to dephosphorylate the polypeptide.

A further aspect of the invention relates to a method for determining the ability of an enzyme, of a functional fragment or derivative thereof to modify the phosphorylation status of a biotinylated polypeptide.

Suitable methods for determining the degree of phosphorylation of biotinylated polypeptides relate for example to methods which are known to be suitable for determining the degree of phosphorylation of short peptides. These are familiar to the skilled worker.

In a preferred embodiment, the method of the invention relates to a method in which the ability of an enzyme, of a functional fragment or derivative thereof to phosphorylate the polypeptide is determined with the following steps:

a) contacting the enzyme or functional fragment or derivative with the biotinylated polypeptide and starting the phosphorylation reaction in a suitable reaction mixture, b) contacting the reaction mixture with a means which is coupled to a carrier and is able to bind to the biotinylated polypeptide, c) determining the phosphorylation state of the polypeptide bound to the means.

A further preferred embodiment of the invention relates to a method for determining the ability of an enzyme, of a functional fragment or derivative thereof to dephosphorylate the polypeptide, with the steps of a) contacting the enzyme or functional fragment or derivative with the biotinylated polypeptide which has at least one phosphate residue, and starting the phosphorylation reaction in a suitable reaction mixture, b) contacting the reaction mixture with a means which is coupled to a carrier and is able to bind the biotinylated polypeptide, c) determining the phosphorylation state of the polypeptide bound to the means.

The means can in this connection be any type of molecule or supramolecular association (e.g. body or device) suitable for binding the biotinylated polypeptide. The binding may in this case take place on the biotin portion or the polypeptide itself, and in the case of binding to the polypeptide itself, a binding which depends on the phosphorylation state is preferred (e.g. binding only in the phosphorylated or unphosphorylated state with reference to single or multiple phosphorylation sites). Preferred embodiments of the means therefore relate to streptavidin or phospho-specific antibodies (i.e. antibodies able to recognize the phosphorylation of particular residues on the polypeptide and to bind specifically to the polypeptide phosphorylated there).

The reaction mixture used for the purposes of the various aspects of the invention may moreover be biochemical (i.e. in vitro) or cellular in nature. The composition of biochemical mixtures depends in this connection on the requirements of the enzyme to be investigated, but suitable constituents and compositions, e.g. ATP, a buffer to adjust a desired pH environment and a desired salt concentration to ensure the enzyme activity, are known to the relevant skilled worker. In the case of biochemical mixtures, it is possible for enzyme and or polypeptide to be present recombinantly and/or as molecule partly or completely purified from natural sources and/or in the form of extracts from biological material, in particular cell or tissue extracts.

Biological material may include inter alia: the cells of a tissue or organ (e.g. brain, blood, liver, spleen, kidney, heart, blood vessels), preferably those of a vertebrate, including humans, or cells from a cell culture. Cells used for the purposes of the invention include in this connection all types of cells, e.g. eukaryotic or prokaryotic unicellular organisms (such as bacteria, e.g. *E. Coli* or yeasts, e.g. *S. pombe* or *s. cerevisiae*) or cell lines derived from multicellular organisms (such as, for example, HeLA, COS, NIH-3T3, CHO, etc.), mammalian cell lines are preferred. Cells of a tissue assemblage or organ of a vertebrate, including humans, can be obtained by conventional techniques such as blood sampling, biopsy or surgical techniques. The preparation of such recombinant molecules, the purification of naturally occurring molecules from cells or tissues and the preparation of cell or tissue extracts is sufficiently well known to the skilled worker (see also examples of the standard literature listed hereinafter).

Cellular systems suitable for use for the purposes of the various aspects are likewise known to the skilled worker and include preferably isolated cells originally derived from tissue assemblages (preferably from vertebrates, particularly preferably mammals and especially humans), particularly preferably in the form of cultivated cell lines; they further include unicellular life forms (eukaryotes or prokaryotes) such as, for example, yeast or bacterial cells, especially in the form of cultivated strains.

Carriers may be all types of molecules or supramolecular associations (e.g. bodies or devices) suitable for removing the peptide coupled to them via the biotin-streptavidin interaction from the reaction mixture, or for labeling this peptide. Suitable devices are, for example, membranes, plates or bodies with a very wide variety of shapes (generally referred to as bead herein), made of various materials sufficiently well known in the prior art. The nature of the carrier depends in this connection on the aim of the method (e.g. diagnostic, finding active substances or discovering new interaction partners) and the mode of detection, and the selection of suitable carriers is within the ability of the skilled worker.

In one embodiment of the method of the invention, radiolabeled γ32P-ATP is added to the reaction mixture, and the phosphorylation state is determined by measuring the radioactivity remaining on the carrier, preferably the membrane or plate, after carrying out at least one washing step. It is possible in this way for the constituents of the reaction mixture which are not bound to streptavidin, including free radioactivity, to be simply removed, so that the phosphorylation state of the polypeptide can be determined simply on the basis of the radioactivity immobilized on the carrier. In this case, the means suitable for binding the biotinylated polypeptide is in particular streptavidin.

In a further preferred embodiment of the method of the invention, an antibody (BSP) able to bind specifically to the phosphorylated polypeptide is added to the reaction mixture. The antibody may in this case both represent the means itself and be added in addition to the means (in which case the latter is then preferably not a phospho-specific antibody and is particularly preferably streptavidin). Determination of the phosphorylation state takes place in this case through determination of the amount of antibody bound to the polypeptide. Suitable procedures for labeling and detecting the antibody are known to the skilled worker. Thus, it is possible on the one hand to employ suitably labeled first antibodies which can be detected directly, or suitably labeled second antibodies directed against the FC (chrystalizing fragment) portion of the first antibody are employed, thus increasing the specificity of detection.

The term antibody includes in this connection both monoclonal antibodies and polyclonal antisera, recombinantly prepared antibodies and recombinantly prepared single-chain antibodies. The selection and preparation of such antibodies is within the ability of the skilled worker, and reference may also be made in this connection to the standard literature listed hereinafter. Suitable labels for such antibodies are also known in the prior art and include, for example, enzymatic labels such as CIP (calf intestinal phosphatase) or HRP (horseradish peroxidase), fluorescent molecules which generate a detectable signal on excitation by irradiation with light of a particular wavelength, such as Texas Red, Cy3, FITC (fluorescein isothiocyanate), or known fluorescent proteins. The selection of suitable labels is likewise in accordance with the ability of the skilled worker. Suitable labeled or unlabeled first and second antibodies, and the preparation thereof, are known prior art and, moreover, such antibodies are commercially available through various suppliers. First and second antibodies can be obtained for example through Becton Dickinson, Pharmacia or Santa Cruz Biotech.

In a preferred embodiment of the above method, the amount of antibody bound to the polypeptide is determined by determining the amount of antibody remaining on the carrier, preferably the membrane or plate, after carrying out at least one washing step.

In a further preferred embodiment of the method of the invention, the carrier coupled to the means is a first carrier which includes a first signal generator, and the polypeptide is coupled to a second carrier which includes a second signal generator, the two signal generators being able to generate a detectable signal when they are in the direct vicinity of one another, and the phosphorylation state is determined by determining whether a detectable signal has been generated. The carriers in this case are preferably beads.

The means here is preferably a phospho-specific antibody. The carrier can in this case be connected directly or indirectly to the antibody, preferably indirectly through protein A which is coupled to the carrier. The second carrier may in this case be linked directly or indirectly to the polypeptide, preferably indirectly through the biotin portion of the biotinylated polypeptide; this preferably takes place via streptavidin coupled to the carrier.

A signal generator may in this case be any type of means or molecule suitable for generating detectable signals; examples include fluorophores which, after excitation by exposure to energy, emit light which can be detected directly or after signal amplification by suitable means which are known in the prior art. The signal generators are in this case chosen for the purposes of the present invention so that a signal is generated only when a direct interaction of the means (i.e. preferably the phospho-specific antibody) with the polypeptide takes place. Suitable carriers and signal generators (e.g. in the form of ALPHAScreen™, or LANCE™, Perkin-Elmer Life Sciences; HTRF™, CIS Bio International)) are known. In these cases, it is crucial for signal generation that the carriers are in the direct vicinity of one another. It is therefore very surprising that this type of method is suitable for use in conjunction with polypeptides, although the latter are distinctly larger than the peptides used in the prior art.

The polypeptide is for the purposes of the various aspects of the present invention preferably the natural substrate of the enzyme, preferably in untruncated length.

Particularly suitable polypeptides include all substrates of the insulin receptor kinase. Particular preference is given in this connection to polypeptides of the insulin receptor substrate (IRS) family, preferably IRS-1, 2, 3 or 4, and IRS-1 or functional fragments or derivatives thereof is particularly preferred. This means fragments or derivatives (or derivatives of fragments) which have the ability to be phosphorylated by the insulin receptor. It is further preferred for the IRS to be human IRS. Furthermore, the use of IRS-1, in particular human IRS-1 with the sequence shown in SEQ ID No. 1 is human IRS-1 encoded by the sequence shown in SEQ ID No. 2, is particularly preferred for the purposes of the various aspects of the present invention. The aforementioned polypeptides are moreover particularly suitable for determining the ability of the insulin receptor to phosphorylate them.

A preferred IRS-1 fragment is a polypeptide having the amino acid sequence shown in SEQ ID No. 3.

The various aspects of the invention can be employed at various levels. Use thereof is particularly expedient in the identification of substances which modify the ability of the enzyme or functional fragment or derivative thereof to modify the phosphorylation state of the polypeptide.

Suitable analytical methods or systems, called assays, which measure the activity or the concentration or amount of particular target molecules of the body (called "targets", in this case the phosphorylation state of the polypeptide) as parameters of the activity of potential active substances are known in the prior art. Possible examples thereof are in vitro assays, i.e. biochemical assays with isolated or partially isolated components which are combined to give a reaction mixture and on the basis of which the activity of potential active substances can be measured. Further possibilities are also cellular assay systems (assays) in which the activity of the target protein (i.e., in the present case, of the enzyme) and the activity of potential active substances on the activity of this target molecule in the cellular environment can be determined.

An assay is in this connection any type of analytical method on the basis of which a biological process can be monitored. This conventionally entails molecular processes and signal cascades which represent parts of physiological metabolic pathways and control mechanisms, but also pathological states, being reproduced in cellular or biochemical systems. The pharmacological activity of an active substance can then be determined on the basis of its ability to intervene in these pathways and mechanisms.

For use for the purposes of finding active substances, in particular of the high throughput screening for active substances, the assay must be reproducible and is preferably also scalable and robust (i.e. has little susceptibility to external influences). The assay should preferably be suitable for high throughput screening of chemical substances for their ability to have an effect on the activity of target molecules. The nature of the assay depends in this connection inter alia on the nature of the target molecule used (e.g. exact type or nature of basic biochemical molecule, e.g. polypeptide or polynucleotide) and the "read out", i.e. the parameters on the basis of which the activity of the target molecule is determined.

Various types of assay are known in the prior art, and most of them are also commercially available from commercial suppliers.

Assays suitable for measuring the interaction of two binding partners include, for example, radioisotopical or fluorescent assays, e.g. fluorescence polarization assays as, for example, commercially available from Panvera, Perkin-Elmer Life Sciences (NEN, LANCE™, AlphaScreen™) or CIS Bio International (HTRF™). Further examples of assays include cellular assays in which a cell line stably (inducibly or constitutively; chromosomally or episomally) or transiently expresses a recombinant protein as desired. These assays include, for example, reporter gene assays in which the regulation of a particular promoter or the regulation of a signal transduction pathway or of a member of a signal transduction cascade is measured on the basis of the activity of a reporter enzyme whose expression is under the control of the relevant promoter. For this type of assay it is necessary to generate a recombinant cell line which expresses the reporter gene under the control of a defined promoter which itself is to be investigated or which is regulated by the signal transduction cascade to be investigated. Suitable reporter enzymes are generally known to the relevant skilled worker and include glow worm luciferase, *Renilla* luciferase (both commercially available for example through Packard Reagents), β-galactosidase, etc. The selection of suitable cell lines is known to the relevant skilled worker and depends inter alia on the aim of the assay or the "read out". These are usually cell lines which are simple to cultivate and to transfect, such as, for example, HeLA, COS, CHO or NIH-3T3 cells.

Suitable for measuring protein phosphorylation or kinase activity are, for example, fluorescence polarization, e.g. commercially available through Panvera, homogeneous time resolved fluorescence (HTRF™, Cis Bio International) or LANCE™ Assays (Perkin-Elmer Life Sciences) or the amplified luminescent proximity homogeneous assay (AL-PHAScreen™ from Perkin-Elmer Life Sciences).

The measurement of the kinase activity using ALPHAScreen™ from Perkin-Elmer Life Sciences, which is particularly expedient for the purposes of the present invention, takes place for example by the kinase to be investigated phosphorylating a biotinylated peptide in a biochemical mixture in the presence of ATP. The phosphorylated peptide is then bound by a specific anti-phospho antibody to which protein A-conjugated acceptor beads or provided with suitable second antibodies are coupled. The same mixture contains streptavidin-coupled donor beads which bind the biotin portion of the peptide. The binding to the peptide brings acceptor beads and donor beads in direct vicinity, starting a cascade of chemical reactions which generate a highly amplified, detectable luminescence signal: a photosensitizer in the donor bead is excited by laser excitation to convert oxygen in the surroundings into a singlet status. The singlet oxygen then diffuses to the acceptor bead where it excites a thioxene derivative which thus emits a chemiluminescence with a wavelength of 370 nm, which in turn excites further fluorophores in the acceptor bead to luminesce light with wavelengths of 520 to 620 nm. Since excitation of the fluorophores by singlet oxygen takes place only when donor bead and acceptor bead are in close vicinity, only then are detectable signals generated.

Other types of assays and other types of "read out" are likewise sufficiently well known to the relevant skilled worker.

Particular preference is given in this connection to use in the form of high throughput methods (HTS, High Throughput Screen) through which a large number of substances can be analyzed in the shortest time.

Depending on the objective, the modification of the modulation may mean an inhibition or activation of the modulation by the enzyme. The nature of the modification includes in this connection all possible influences eventually having an effect on the enzyme-catalyzed phosphorylation state of the polypeptide, such as modification of the enzyme-substrate interaction or modification of the catalytical activity of the enzyme, but also (preferably in the case of analysis using cellular reaction mixtures) modification of enzyme expression, etc.

A further aspect of the invention relates to a method for identifying substances which modify the ability of an enzyme or functional fragment or derivative thereof to modify the phosphorylation state of a polypeptide, with the steps of a) determining the ability of the enzyme or functional fragment or derivative thereof to modify the phosphorylation state of the polypeptide in accordance with one of the aforementioned methods of the invention, without addition of the substance to be tested to the reaction mixture, b) determining the ability of the enzyme or functional fragment or derivative thereof to modify the phosphorylation state of the polypeptide in accordance with one of the above-described methods of the invention, with addition of the substance to be tested to the reaction mixture, c) comparing the ability from a) with that from b).

The methods of the invention are particularly suitable for identifying pharmacologically active substances for the treatment of non-insulin-dependent diabetes mellitus (NIDDM), in oncology (IGFRK) or for the treatment of inflammatory processes (IKK kinase). The invention is explained in more detail below by means of various figures and examples without restricting the subject matter of the invention thereby.

EXAMPLES

Example 1

IRS-1 Fragment Used

To demonstrate the possibility of biotinylating a polypeptide substrate from the insulin signal pathway and employing it for the uses and methods of the invention, a fragment 262 amino acids in size from human IRS-1 was chosen (aa516-aa777), which encodes central potential tyrosine (bold) and serine phosphorylation sites (underlined) (Siemeister et al. J. Biol. Chem. 1995). The fragment comprises five potential tyrosine phosphorylation sites, which are emphasized in FIG. 3 and shown in bold hereinafter together with their motifs.

```
516 -
DLDNRFRKRT HSAGTSPTIT HQKTPSQSSV ASIEEYTEMM

PAYPPGGGSG GRLPGHRHSA FVPTRSYPEE GLEMHPLERR

GGHHRPDSST LHTDDGYMPM SPGVAPVPSG RKGSGDYMPM

SPKSVSAPQQ IINPIRRHPQ RVDPNGYMMM SPSGGCSPDI

GGGPSSSSSS SNAVPSGTSY GKLWTNGVGG HHSHVLPHPK

PPVESSGGKL LPCTGDYMNM SPVGDSNTSS PSDCYYGPED

PQHKPVLSYY SLPRSFKHTQ RP -777
```

The serines 612, 632, 662 and 731, which represent four possible serine kinase phosphorylation sites in YMXMSP motifs are located near the tyrosine phosphorylation sites of the insulin receptor, which are accommodated in binding sites for SH2 domains. Mutation of these serine residues to alanine leads to an increase in the IRS-1-mediated activity of phosphatidyl-insositol trisphosphate kinase (PI3K), (Mothe et al. 1996), which indicates that they have an inhibiting function. However, it cannot be precluded that further serine phosphorylation sites are also present but are as yet unknown.

Example 2

Cloning and biotinylation of hIRS-1-p30

For the investigation, the 262 amino acids-long domain D516-P777 (hIRS-1-p30) of human IRS-1 was initially expressed in *E-coli* as described in Siemeister et al., 1995. The expression vectors were in this case prepared by customary methods by inserting the polynucleotide with the sequence shown in SEQ ID No. 10 (cDNA sequence of hIRS-1-p30) into the plasmid pET3d (commercially available under the order number 69421 from Novagen). For this purpose, firstly the empty vector was digested with the enzymes in NcoI (commercially available from Roche Diagnostics GmbH Mannheim under order number 835315) and BamHI (commercially available from Roche Diagnostics GmbH Mannheim under order number 656275) under standard conditions and purified using spin columns (commercially available from Qiagen, Hilden under order number 28104).

The biotinylation took place in this case under contract by the commercial supplier N-Zyme, Darmstadt, Germany using conventional techniques. Expression of the hIRS-1-p30 insulin receptor fragment took place as described in Siemeister et al., 1995. To check the results of expression, protein extracts from *E. coli* (strain *E. coli* BL21, commercially available from Novagen under order number 69451-3) were prepared, fractionated by SDS-PAGE under standard conditions (see, for example, the standard literature listed hereinafter) and demonstrated by staining with Coomassie stain solution under standard conditions (see, for example, standard literature listed hereinafter). The purification of hIRS-1-p30 likewise took place in accordance with Siemeister et. al. Biotinylation of hIRS-1-p30 took place enzymatically using transglutaminase.

Example 3

ALPHAScreen™: Phosphorylation of Biotinylated IRS-1 Fragment by Wheat Germ Lectin Affinity-purified Rat Liver Insulin Receptor In the experiment whose result is depicted in FIG. 4, rat liver insulin receptor purified by wheat germ lectin affinity chromatography (WGA-IR, SEQACC number NP_058767 or commercially available from Sigma under order number 70543) was incubated with various concentrations of human insulin (e.g. commercially available from Sigma under order number I-9266) and 85 nM biotinylated IRS fragment in 50 mM Tris buffer, pH 7.4, 8 mM MgCl2, 2 mM MnCl2 at 4° C. for 10 minutes, followed by incubation at 30° C. for 30 minutes after addition of ATP (final concentration 50 µM). The reaction was then stopped by adding EDTA to a final concentration of 20 mM, and the phosphorylation of IRS-1 was detected by using a specific antibody directly coupled to the acceptor p-Tyr (commercially available through Perkin-Elmer Life Sciences under order number 6760601C), which resulted in the readout depicted in FIG. 4. It was possible with the aid of this method to determine EC50 for insulin to be 10 nM.

Example 4

ALPHAScreen™: Phosphorylation of Biotinylated IRS-1 Fragment by PKC and Recombinant Insulin Receptor Kinase ALPHAScreen™ from Perkin-Elmer Life Sciences makes it possible to detect the interaction between the phosphorylated IRS-1 fragment and antibodies which recognize phosphorylated serine or tyrosine residues (p-Ser/p-Tyr antibodies). Biotinylated IRS-1 is in this case bound to the streptavidin donor, and the antibody is bound by acceptor-coupled protein A or a suitable second antibody bound to the acceptor. If an interaction takes place, the acceptor arrives and remains in the direct vicinity of the donor, so that singlet oxygen atoms generated by the donor are able by diffusion to reach chemiluminescent groups in the acceptor bead, which ultimately results in the emission of detectable light.

Figure 5A:
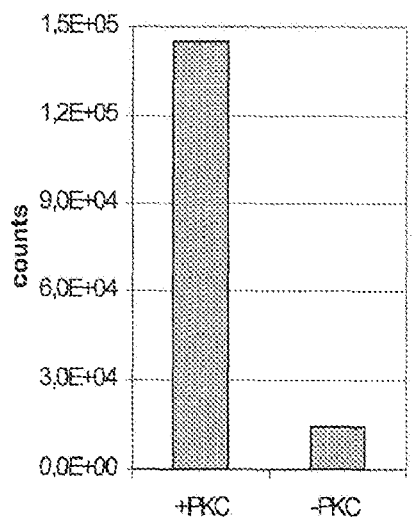
Figure 5B:
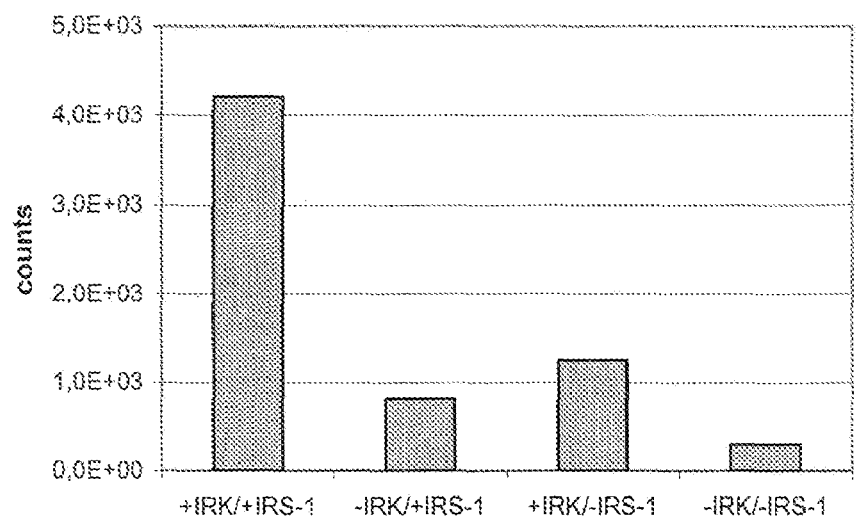
Figure 6:
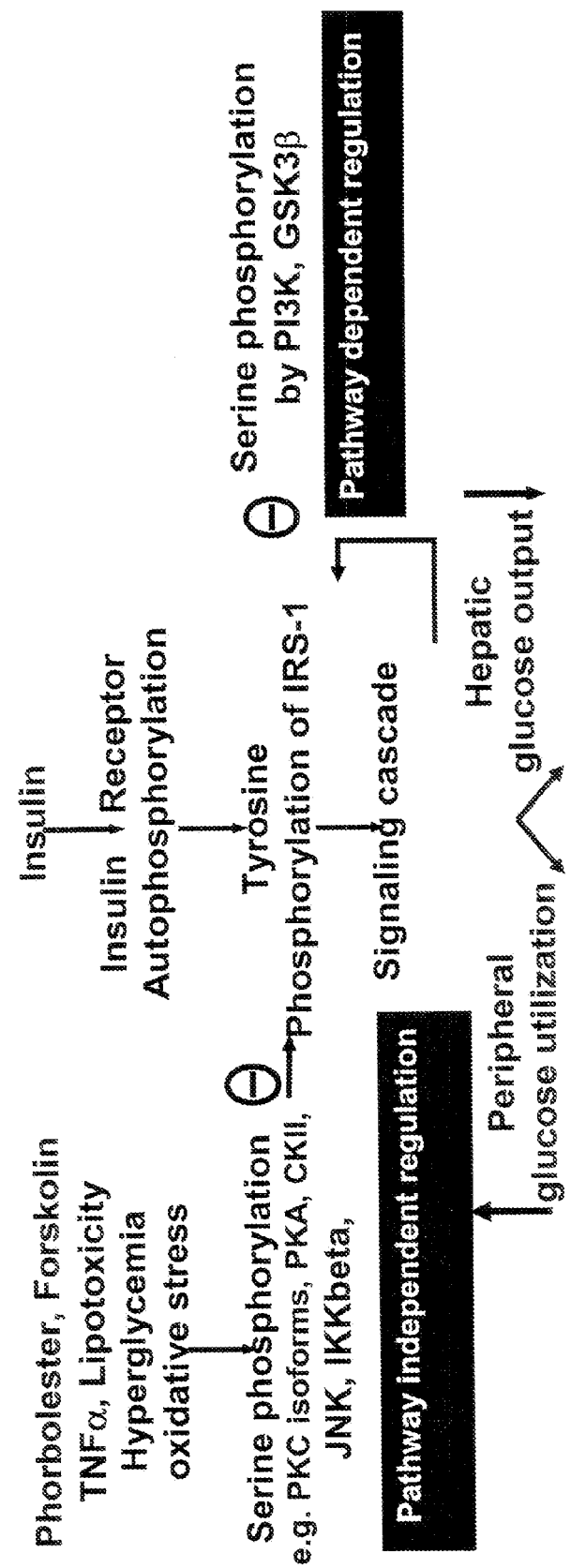
Figure 7:
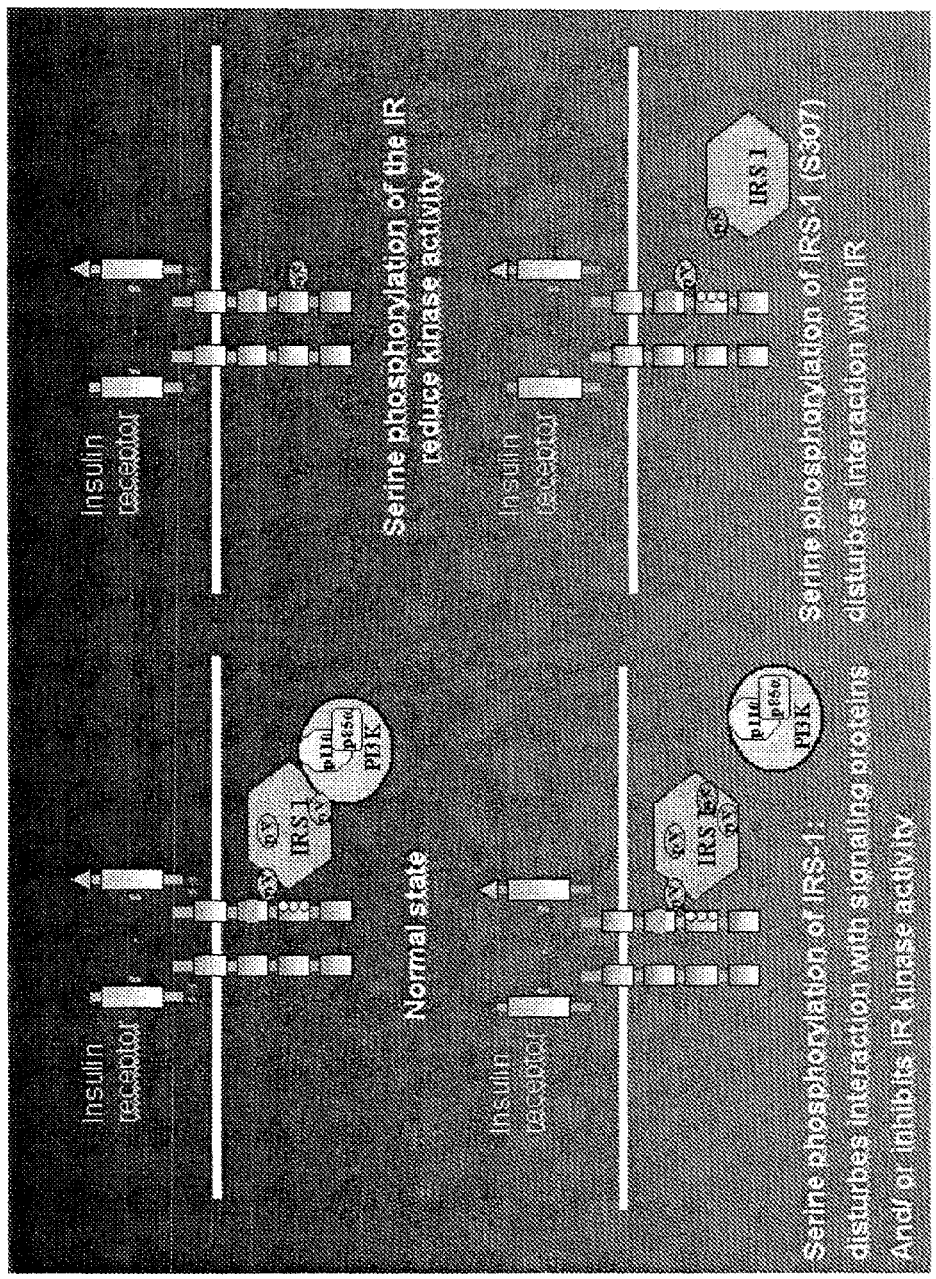
FIG. 7 summarizes the possible molecular mechanisms of serine phosphorylation having an inhibitory effect.

The light intensities (the so-called "readout") generated in the aforementioned assay and depicted in the form of bar diagrams in FIG. 5A and B were detected and quantified after incubation of IRS-1 with protein kinase C and ATP for 30 minutes and subsequent addition of p Ser antibodies (commercially available from Biosource, Belgium under order number 44-550) and further incubation for 120 minutes by measurement with a Perkin-Elmer Fusion or AlphaQuest instrument. Comparison of the generated light intensities in the presence and in the absence of PKC is depicted in FIG. 5A. In the experiment whose result is depicted in FIG. 5B, recombinant insulin receptor kinase (IRK, amino acid 941-1343, NCBI access number $NM_{13}000208$) was activated by incubating with polylysine in 50 mM Tris buffer, pH 7.4, 8 mM MgCl2, 50 µM ATP reaction buffer at 30° C. for 10 minutes and then the IRK substrate IRS was added, followed by incubation at 30° C. for 30 minutes. The phosphorylation of IRS 1 was detected using a p Tyr specific antibody (commercially available through Perkin-Elmer Life Sciences under order number 6760601C) coupled directly to the acceptor, resulting in the readout depicted in FIG. 5B.

The foregoing examples show that the inventors were able to demonstrate, for the first time, that biotinylated polypeptides can be phosphorylated by kinases. This was demonstrated by means of a hIRS-1 fragment 28 kDA in size which can be phosphorylated in the biotinylated state by the serine kinase PKCδ and by the tyrosine kinase of the insulin receptor. Detection by phospho-specific antibodies was in this case likewise successful without interference with the detection reaction through steric hindrance owing to the size of the polypeptide in conjunction with the biotin residue. It was possible thereby, based on the principle of the ALPHAScreen™, to generate a homogeneous assay system with which it is possible to determine the phosphorylation state of polypeptides using the purification and detection techniques possible owing to the biotinylation. This assay principle was applied here for the first time to a protein fragment with the size of a polypeptide (more accurately 28 kDa). This makes possible an improved search for pharmacologically active substances which interact with the phosphorylation and dephosphorylation machinery of the cell-diagnosis of phosphorylation-dependent disorders/identification of novel protein kinases for specific polypeptides on large and even structurally intact physiological substrates, thus considerably increasing the specificity of the phosphorylations or dephosphorylations on which these investigations are based, and thus the information provided by the data generated in this way. In addition, the readout in the assay system used herein was non-radioactive, but luminescent, which represents an advantage for the use in high throughput screening (HTS) methods. The assay described herein can thus be employed for the HTS of all enzymes which modify the phosphorylation status of polypeptides and proteins, such as kinases and phosphatases, for the identification of novel active substances or verification of known active substances. It is likewise suitable for other methods such as the aforementioned methods for searching for novel enzymes which phosphorylate particular polypeptides, for example novel IRS-1 phosphorylating kinases in whole cell lysates.

The invention claimed is:

1. A method for determining the ability of a first polypeptide to modify the phosphorylation status of a second, biotinylated polypeptide, the method comprising the steps of
   a. contacting the first polypeptide with the second polypeptide in a suitable reaction mixture;
   b. contacting the reaction mixture with a means which is coupled to a carrier and is able to bind to the second polypeptide; and
   c. determining the phosphorylation state of the second polypeptide,
wherein the carrier comprises a first carrier and a second carrier, wherein the first carrier comprises a first signal generator and the second carrier comprises a second signal generator, wherein the first carrier is coupled to the means and the second carrier is coupled to the second polypeptide.

2. The method of claim 1, wherein the means comprises a phospho-specific antibody.

3. The method of claim 1, wherein the means comprise streptavidin.

4. The method of claim 1, wherein the step of determining the phosphorylation state comprises determining whether a signal has been generated.

5. The method of claim 1, wherein the second polypeptide has a length of at least about 50 amino acids.

6. The method of claim 5, wherein the second polypeptide has a length of about 50 to 300 amino acids.

7. The method of claim 6, wherein the second polypeptide has a size of at least about 1 to 100 kda.

8. The method of claim 6, wherein the second polypeptide has a size of about 10 to 50 kda.

9. The method of claim 6, wherein the second polypeptide has a size of about 25 to 35 kda.

10. The method of claim 1, wherein the first polypeptide is an enzyme.

11. The method of claim 10, wherein the first polypeptide is a kinase.

12. The method of claim 11, wherein the first polypeptide is a tyrosine kinase.

13. The method of claim 1, wherein the first polypeptide is insulin receptor, IGF-1 receptor, trK receptor, EGF receptor, casein kinase II, protein kinase C, protein kinase B/Akt, mitogen-activated protein kinase (MAP kinase), GSK-3, ERK, JNK, or a functional fragment of any of the foregoing.

14. The method of claim 1, wherein the first polypeptide is a functional fragment of an enzyme or a functional derivative of an enzyme.

15. The method of claim 1, wherein the second polypeptide is a natural substrate of the first polypeptide.

* * * * *

UNITED STATES PATENT AND TRADEMARK OFFICE
CERTIFICATE OF CORRECTION

| | | |
|---|---|---|
| PATENT NO. | : 7,732,151 B2 | Page 1 of 1 |
| APPLICATION NO. | : 10/849424 | |
| DATED | : June 8, 2010 | |
| INVENTOR(S) | : Norbert Tennagels et al. | |

It is certified that error appears in the above-identified patent and that said Letters Patent is hereby corrected as shown below:

In column 1, line 32, delete "and or" and insert -- and/or --, therefor.

In column 2, line 4, delete "plextrin" and insert -- Pleckstrin --, therefor.

In column 4, line 7, delete "NM_03604" and insert -- NM_003604 --, therefor.

In column 4, line 20, after "chromatography" insert -- . --.

In column 6, line 30, delete "and or" and insert -- and/or --, therefor.

In column 7, line 31, delete "(chrystalizing" and insert -- (crystallizing --, therefor.

In column 11, line 28, delete "-insositol" and insert -- -inositol --, therefor.

In column 12, line 51, delete "p Ser" and insert -- p-Ser --, therefor.

In column 12, line 59, delete "$NM_{13}000208$)" and insert -- NM_000208) --, therefor.

In column 12, line 61, delete "MgCl2," and insert -- $MgCl_2$, --, therefor.

Signed and Sealed this
Twenty-fifth Day of January, 2011

David J. Kappos
*Director of the United States Patent and Trademark Office*

SEQUENCE LISTING

```
<160> NUMBER OF SEQ ID NOS: 9

<210> SEQ ID NO 1
<211> LENGTH: 1242
<212> TYPE: PRT
<213> ORGANISM: Homo sapiens

<400> SEQUENCE: 1

Met Ala Ser Pro Pro Glu Ser Asp Gly Phe Ser Asp Val Arg Lys Val
 1               5                  10                  15

Gly Tyr Leu Arg Lys Pro Lys Ser Met His Lys Arg Phe Phe Val Leu
                20                  25                  30

Arg Ala Ala Ser Glu Ala Gly Gly Pro Ala Arg Leu Glu Tyr Tyr Glu
            35                  40                  45

Asn Glu Lys Lys Trp Arg His Lys Ser Ser Ala Pro Lys Arg Ser Ile
        50                  55                  60

Pro Leu Glu Ser Cys Phe Asn Ile Asn Lys Arg Ala Asp Ser Lys Asn
 65                  70                  75                  80

Lys His Leu Val Ala Leu Tyr Thr Arg Asp Glu His Phe Ala Ile Ala
                85                  90                  95

Ala Asp Ser Glu Ala Glu Gln Asp Ser Trp Tyr Gln Ala Leu Leu Gln
            100                 105                 110

Leu His Asn Arg Ala Lys Gly His His Asp Gly Ala Ala Ala Leu Gly
        115                 120                 125

Ala Gly Gly Gly Gly Ser Cys Ser Gly Ser Ser Gly Leu Gly Glu
    130                 135                 140

Ala Gly Glu Asp Leu Ser Tyr Gly Asp Val Pro Pro Gly Pro Ala Phe
145                 150                 155                 160

Lys Glu Val Trp Gln Val Ile Leu Lys Pro Lys Gly Leu Gly Gln Thr
                165                 170                 175

Lys Asn Leu Ile Gly Ile Tyr Arg Leu Cys Leu Thr Ser Lys Thr Ile
            180                 185                 190

Ser Phe Val Lys Leu Asn Ser Glu Ala Ala Ala Val Val Leu Gln Leu
        195                 200                 205

Met Asn Ile Arg Arg Cys Gly His Ser Glu Asn Phe Phe Ile Glu
    210                 215                 220
```

-continued

```
Val Gly Arg Ser Ala Val Thr Gly Pro Gly Glu Phe Trp Met Gln Val
225                 230                 235                 240

Asp Asp Ser Val Val Ala Gln Asn Met His Glu Thr Ile Leu Glu Ala
            245                 250                 255

Met Arg Ala Met Ser Asp Glu Phe Arg Pro Arg Ser Lys Ser Gln Ser
        260                 265                 270

Ser Ser Asn Cys Ser Asn Pro Ile Ser Val Pro Leu Arg Arg His His
    275                 280                 285

Leu Asn Asn Pro Pro Pro Ser Gln Val Gly Leu Thr Arg Arg Ser Arg
    290                 295                 300

Thr Glu Ser Ile Thr Ala Thr Ser Pro Ala Ser Met Val Gly Gly Lys
305                 310                 315                 320

Pro Gly Ser Phe Arg Val Arg Ala Ser Ser Asp Gly Glu Gly Thr Met
            325                 330                 335

Ser Arg Pro Ala Ser Val Asp Gly Ser Pro Val Ser Pro Ser Thr Asn
        340                 345                 350

Arg Thr His Ala His Arg His Arg Gly Ser Ala Arg Leu His Pro Pro
    355                 360                 365

Leu Asn His Ser Arg Ser Ile Pro Met Pro Ala Ser Arg Cys Ser Pro
    370                 375                 380

Ser Ala Thr Ser Pro Val Ser Leu Ser Ser Ser Thr Ser Gly His
385                 390                 395                 400

Gly Ser Thr Ser Asp Cys Leu Phe Pro Arg Arg Ser Ala Ser Val
            405                 410                 415

Ser Gly Ser Pro Ser Asp Gly Gly Phe Ile Ser Ser Asp Glu Tyr Gly
        420                 425                 430

Ser Ser Pro Cys Asp Phe Arg Ser Phe Arg Ser Val Thr Pro Asp
    435                 440                 445

Ser Leu Gly His Thr Pro Pro Ala Arg Gly Glu Glu Glu Leu Ser Asn
    450                 455                 460

Tyr Ile Cys Met Gly Gly Lys Gly Pro Ser Thr Leu Thr Ala Pro Asn
465                 470                 475                 480

Gly His Tyr Ile Leu Ser Arg Gly Asn Gly His Arg Cys Thr Pro
            485                 490                 495

Gly Thr Gly Leu Gly Thr Ser Pro Ala Leu Ala Gly Asp Glu Ala Ala
        500                 505                 510

Ser Ala Ala Asp Leu Asp Asn Arg Phe Arg Lys Arg Thr His Ser Ala
    515                 520                 525

Gly Thr Ser Pro Thr Ile Thr His Gln Lys Thr Pro Ser Gln Ser Ser
    530                 535                 540

Val Ala Ser Ile Glu Glu Tyr Thr Glu Met Met Pro Ala Tyr Pro Pro
545                 550                 555                 560

Gly Gly Gly Ser Gly Gly Arg Leu Pro Gly His Arg His Ser Ala Phe
            565                 570                 575

Val Pro Thr Arg Ser Tyr Pro Glu Glu Gly Leu Glu Met His Pro Leu
        580                 585                 590

Glu Arg Arg Gly Gly His His Arg Pro Asp Ser Ser Thr Leu His Thr
    595                 600                 605

Asp Asp Gly Tyr Met Pro Met Ser Pro Gly Val Ala Pro Val Pro Ser
    610                 615                 620

Gly Arg Lys Gly Ser Gly Asp Tyr Met Pro Met Ser Pro Lys Ser Val
625                 630                 635                 640

Ser Ala Pro Gln Gln Ile Ile Asn Pro Ile Arg Arg His Pro Gln Arg
```

-continued

```
                645                 650                 655
Val Asp Pro Asn Gly Tyr Met Met Ser Pro Ser Gly Gly Cys Ser
                660                 665                 670
Pro Asp Ile Gly Gly Gly Pro Ser Ser Ser Ser Ser Ser Asn Ala
                675                 680                 685
Val Pro Ser Gly Thr Ser Tyr Gly Lys Leu Trp Thr Asn Gly Val Gly
                690                 695                 700
Gly His His Ser His Val Leu Pro His Pro Lys Pro Val Glu Ser
705                 710                 715                 720
Ser Gly Gly Lys Leu Leu Pro Cys Thr Gly Asp Tyr Met Asn Met Ser
                725                 730                 735
Pro Val Gly Asp Ser Asn Thr Ser Ser Pro Ser Asp Cys Tyr Tyr Gly
                740                 745                 750
Pro Glu Asp Pro Gln His Lys Pro Val Leu Ser Tyr Tyr Ser Leu Pro
                755                 760                 765
Arg Ser Phe Lys His Thr Gln Arg Pro Gly Glu Pro Glu Glu Gly Ala
                770                 775                 780
Arg His Gln His Leu Arg Leu Ser Thr Ser Ser Gly Arg Leu Leu Tyr
785                 790                 795                 800
Ala Ala Thr Ala Asp Asp Ser Ser Ser Thr Ser Ser Asp Ser Leu
                805                 810                 815
Gly Gly Gly Tyr Cys Gly Ala Arg Leu Glu Pro Ser Leu Pro His Pro
                820                 825                 830
His His Gln Val Leu Gln Pro His Leu Pro Arg Lys Val Asp Thr Ala
                835                 840                 845
Ala Gln Thr Asn Ser Arg Leu Ala Arg Pro Thr Arg Leu Ser Leu Gly
850                 855                 860
Asp Pro Lys Ala Ser Thr Leu Pro Arg Ala Arg Glu Gln Gln Gln Gln
865                 870                 875                 880
Gln Gln Pro Leu Leu His Pro Pro Glu Pro Lys Ser Pro Gly Glu Tyr
                885                 890                 895
Val Asn Ile Glu Phe Gly Ser Asp Gln Ser Gly Tyr Leu Ser Gly Pro
                900                 905                 910
Val Ala Phe His Ser Ser Pro Ser Val Arg Cys Pro Ser Gln Leu Gln
                915                 920                 925
Pro Ala Pro Arg Glu Glu Thr Gly Thr Glu Tyr Met Lys Met
                930                 935                 940
Asp Leu Gly Pro Gly Arg Arg Ala Ala Trp Gln Glu Ser Thr Gly Val
945                 950                 955                 960
Glu Met Gly Arg Leu Gly Pro Ala Pro Pro Gly Ala Ala Ser Ile Cys
                965                 970                 975
Arg Pro Thr Arg Ala Val Pro Ser Ser Arg Gly Asp Tyr Met Thr Met
                980                 985                 990
Gln Met Ser Cys Pro Arg Gln Ser Tyr Val Asp Thr Ser Pro Ala Ala
                995                 1000                1005
Pro Val Ser Tyr Ala Asp Met Arg Thr Gly Ile Ala Ala Glu Glu Val
    1010                1015                1020
Ser Leu Pro Arg Ala Thr Met Ala Ala Ala Ser Ser Ser Ser Ala Ala
1025                1030                1035                1040
Ser Ala Ser Pro Thr Gly Pro Gln Gly Ala Ala Glu Leu Ala Ala His
                1045                1050                1055
Ser Ser Leu Leu Gly Gly Pro Gln Gly Pro Gly Gly Met Ser Ala Phe
                1060                1065                1070
```

```
Thr Arg Val Asn Leu Ser Pro Asn Arg Asn Gln Ser Ala Lys Val Ile
    1075                1080                1085

Arg Ala Asp Pro Gln Gly Cys Arg Arg His Ser Ser Glu Thr Phe
    1090                1095                1100

Ser Ser Thr Pro Ser Ala Thr Arg Val Gly Asn Thr Val Pro Phe Gly
1105                1110                1115                1120

Ala Gly Ala Ala Val Gly Gly Gly Gly Ser Ser Ser Ser Glu
            1125                1130                1135

Asp Val Lys Arg His Ser Ser Ala Ser Phe Glu Asn Val Trp Leu Arg
            1140                1145                1150

Pro Gly Glu Leu Gly Gly Ala Pro Lys Glu Pro Ala Lys Leu Cys Gly
    1155                1160                1165

Ala Ala Gly Gly Leu Glu Asn Gly Leu Asn Tyr Ile Asp Leu Asp Leu
    1170                1175                1180

Val Lys Asp Phe Lys Gln Cys Pro Gln Glu Cys Thr Pro Glu Pro Gln
1185                1190                1195                1200

Pro Pro Pro Pro Pro Pro His Gln Pro Leu Gly Ser Gly Glu Ser
            1205                1210                1215

Ser Ser Thr Arg Arg Ser Ser Glu Asp Leu Ser Ala Tyr Ala Ser Ile
            1220                1225                1230

Ser Phe Gln Lys Gln Pro Glu Asp Arg Gln
    1235                1240

<210> SEQ ID NO 2
<211> LENGTH: 1324
<212> TYPE: PRT
<213> ORGANISM: Homo sapiens

<400> SEQUENCE: 2

Met Ala Ser Pro Pro Arg His Gly Pro Pro Gly Pro Ala Ser Gly Asp
  1               5                  10                  15

Gly Pro Asn Leu Asn Asn Asn Asn Asn Asn Asn His Ser Val Arg
                20                  25                  30

Lys Cys Gly Tyr Leu Arg Lys Gln Lys His Gly His Lys Arg Phe Phe
            35                  40                  45

Val Leu Arg Gly Pro Gly Ala Gly Gly Asp Lys Ala Thr Ala Gly Gly
        50                  55                  60

Gly Ser Ala Pro Gln Pro Pro Arg Leu Glu Tyr Tyr Glu Ser Glu Lys
65                  70                  75                  80

Asn Trp Arg Ser Lys Ala Gly Ala Pro Lys Arg Val Ile Ala Leu Asp
                85                  90                  95

Cys Cys Leu Asn Ile Asn Lys Arg Ala Asp Pro Lys His Lys Tyr Leu
            100                 105                 110

Ile Ala Leu Tyr Thr Lys Asp Glu Tyr Phe Ala Val Ala Ala Glu Asn
        115                 120                 125

Glu Gln Glu Gln Glu Gly Trp Tyr Arg Ala Leu Thr Asp Leu Val Ser
    130                 135                 140

Glu Gly Arg Ala Ala Ala Gly Asp Ala Pro Pro Ala Ala Ala Pro Ala
145                 150                 155                 160

Ala Ser Cys Ser Ala Ser Leu Pro Gly Ala Val Gly Ser Ala Gly
                165                 170                 175

Ala Ala Gly Ala Glu Asp Ser Tyr Gly Leu Val Ala Pro Ala Thr Ala
            180                 185                 190

Ala Tyr Arg Glu Val Trp Gln Val Asn Leu Lys Pro Lys Gly Leu Gly
```

-continued

```
            195                 200                 205
Gln Ser Lys Asn Leu Thr Gly Val Tyr Arg Leu Cys Leu Ser Ala Arg
    210                 215                 220

Thr Ile Gly Phe Val Lys Leu Asn Cys Glu Gln Pro Ser Val Thr Leu
225                 230                 235                 240

Gln Leu Met Asn Ile Arg Arg Cys Gly His Ser Asp Ser Phe Phe Phe
                245                 250                 255

Ile Glu Val Gly Arg Ser Ala Val Thr Gly Pro Gly Glu Leu Trp Met
                260                 265                 270

Gln Ala Asp Asp Ser Val Val Ala Gln Asn Ile His Glu Thr Ile Leu
            275                 280                 285

Glu Ala Met Lys Ala Leu Lys Glu Leu Phe Glu Phe Arg Pro Arg Ser
        290                 295                 300

Lys Ser Gln Ser Ser Gly Ser Ser Ala Thr His Pro Ile Ser Val Pro
305                 310                 315                 320

Gly Ala Arg Arg His His His Leu Val Asn Leu Pro Pro Ser Gln Thr
                325                 330                 335

Gly Leu Val Arg Arg Ser Arg Thr Asp Ser Leu Ala Ala Thr Pro Pro
                340                 345                 350

Ala Ala Lys Cys Ser Ser Cys Arg Val Arg Thr Ala Ser Glu Gly Asp
            355                 360                 365

Gly Gly Ala Ala Ala Gly Ala Ala Ala Gly Ala Arg Pro Val Ser
        370                 375                 380

Val Ala Gly Ser Pro Leu Ser Pro Gly Pro Val Arg Ala Pro Leu Ser
385                 390                 395                 400

Arg Ser His Thr Leu Ile Gly Gly Cys Arg Ala Ala Gly Thr Lys Trp
                405                 410                 415

His Cys Phe Pro Ala Gly Gly Leu Gln His Ser Arg Ser Met Ser
                420                 425                 430

Met Pro Val Glu His Leu Pro Pro Ala Ala Thr Ser Pro Gly Ser Leu
            435                 440                 445

Ser Ser Ser Ser Asp His Gly Trp Gly Ser Tyr Pro Pro Pro Gly
450                 455                 460

Pro His Pro Leu Leu Pro His Pro Leu His His Gly Pro Gly Gln Arg
465                 470                 475                 480

Pro Ser Ser Gly Ser Ala Ser Ala Ser Gly Ser Pro Ser Asp Pro Gly
                485                 490                 495

Phe Met Ser Leu Asp Glu Tyr Gly Ser Ser Pro Gly Asp Leu Arg Ala
            500                 505                 510

Phe Cys Ser His Arg Ser Asn Thr Pro Glu Ser Ile Ala Glu Thr Pro
            515                 520                 525

Pro Ala Arg Asp Gly Gly Gly Gly Glu Phe Tyr Gly Tyr Met Thr
        530                 535                 540

Met Asp Arg Pro Leu Ser His Cys Gly Arg Ser Tyr Arg Arg Val Ser
545                 550                 555                 560

Gly Asp Ala Ala Gln Asp Leu Asp Arg Gly Leu Arg Lys Arg Thr Tyr
                565                 570                 575

Ser Leu Thr Thr Pro Ala Arg Gln Arg Pro Val Pro Gln Pro Ser Ser
                580                 585                 590

Ala Ser Leu Asp Glu Tyr Thr Leu Met Arg Ala Thr Phe Ser Gly Ser
            595                 600                 605

Ala Gly Arg Leu Cys Pro Ser Cys Pro Ala Ser Ser Pro Lys Val Ala
            610                 615                 620
```

```
Tyr His Pro Tyr Pro Glu Asp Tyr Gly Asp Ile Glu Ile Gly Ser His
625                 630                 635                 640

Arg Ser Ser Ser Asn Leu Gly Ala Asp Asp Gly Tyr Met Pro Met
            645                 650                 655

Thr Pro Gly Ala Ala Leu Ala Gly Ser Gly Ser Gly Ser Cys Arg Ser
                660                 665                 670

Asp Asp Tyr Met Pro Met Ser Pro Ala Val Ser Ala Pro Lys Gln
            675                 680                 685

Ile Leu Gln Pro Arg Ala Ala Ala Ala Ala Ala Ala Val Pro Phe
            690                 695                 700

Ala Gly Pro Ala Gly Pro Ala Pro Thr Phe Ala Ala Gly Arg Thr Phe
705                 710                 715                 720

Pro Ala Ser Gly Gly Gly Tyr Lys Ala Ser Ser Pro Ala Glu Ser Ser
                725                 730                 735

Pro Glu Asp Ser Gly Tyr Met Arg Met Trp Cys Gly Ser Lys Leu Ser
            740                 745                 750

Met Glu His Ala Asp Gly Lys Leu Leu Pro Asn Gly Asp Tyr Leu Asn
            755                 760                 765

Val Ser Pro Ser Asp Ala Val Thr Thr Gly Thr Pro Pro Asp Phe Phe
770                 775                 780

Ser Ala Ala Leu His Pro Gly Gly Glu Pro Leu Arg Gly Val Pro Gly
785                 790                 795                 800

Cys Cys Tyr Ser Ser Leu Pro Arg Ser Tyr Lys Ala Pro Tyr Thr Cys
                805                 810                 815

Gly Gly Asp Ser Asp Gln Tyr Val Leu Met Ser Ser Pro Val Gly Arg
            820                 825                 830

Ile Leu Glu Glu Arg Leu Glu Pro Gln Ala Thr Pro Gly Pro Thr
            835                 840                 845

Gln Ala Ala Ser Ala Phe Gly Ala Gly Pro Thr Gln Pro Pro His Pro
850                 855                 860

Val Val Pro Ser Pro Val Arg Pro Ser Gly Gly Arg Pro Glu Gly Phe
865                 870                 875                 880

Leu Gly Gln Arg Gly Arg Ala Val Arg Pro Thr Arg Leu Ser Leu Glu
            885                 890                 895

Gly Leu Pro Ser Leu Pro Ser Met His Glu Tyr Pro Leu Pro Pro Glu
            900                 905                 910

Pro Lys Ser Pro Gly Glu Tyr Ile Asn Ile Asp Phe Gly Glu Pro Gly
            915                 920                 925

Ala Arg Leu Ser Pro Pro Ala Pro Pro Leu Leu Ala Ser Ala Ser
    930                 935                 940

Ser Ser Ser Leu Leu Ser Ala Ser Ser Pro Ala Leu Ser Leu Gly Ser
945                 950                 955                 960

Gly Thr Pro Gly Thr Ser Ser Asp Ser Arg Gln Arg Ser Pro Leu Ser
                965                 970                 975

Asp Tyr Met Asn Leu Asp Phe Ser Ser Pro Lys Ser Pro Lys Pro Gly
            980                 985                 990

Ala Pro Ser Gly His Pro Val Gly Ser Leu Asp Gly Leu Leu Ser Pro
        995                 1000                1005

Glu Ala Ser Ser Pro Tyr Pro Pro Leu Pro Pro Arg Pro Ser Ala Ser
    1010                1015                1020

Pro Ser Ser Ser Leu Gln Pro Pro Pro Pro Pro Ala Pro Gly Glu
1025                1030                1035                1040
```

```
Leu Tyr Arg Leu Pro Pro Ala Ser Ala Val Ala Thr Ala Gln Gly Pro
            1045                1050                1055

Gly Ala Ala Ser Ser Leu Ser Ser Asp Thr Gly Asp Asn Gly Asp Tyr
        1060                1065                1070

Thr Glu Met Ala Phe Gly Val Ala Ala Thr Pro Pro Gln Pro Ile Ala
    1075                1080                1085

Ala Pro Pro Lys Pro Glu Ala Ala Arg Val Ala Ser Pro Thr Ser Gly
        1090                1095                1100

Val Lys Arg Leu Ser Leu Met Glu Gln Val Ser Gly Val Glu Ala Phe
1105                1110                1115                1120

Leu Gln Ala Ser Gln Pro Pro Asp Pro His Arg Gly Ala Lys Val Ile
            1125                1130                1135

Arg Ala Asp Pro Gln Gly Gly Arg Arg Arg His Ser Ser Glu Thr Phe
        1140                1145                1150

Ser Ser Thr Thr Thr Val Thr Pro Val Ser Pro Ser Phe Ala His Asn
        1155                1160                1165

Pro Lys Arg His Asn Ser Ala Ser Val Glu Asn Val Ser Leu Arg Lys
    1170                1175                1180

Ser Ser Glu Gly Gly Val Gly Val Gly Pro Gly Gly Asp Glu Pro
1185                1190                1195                1200

Pro Thr Ser Pro Arg Gln Leu Gln Pro Ala Pro Pro Leu Ala Pro Gln
        1205                1210                1215

Gly Arg Pro Trp Thr Pro Gly Gln Pro Gly Gly Leu Val Gly Cys Pro
        1220                1225                1230

Gly Ser Gly Gly Ser Pro Met Arg Arg Glu Thr Ser Ala Gly Phe Gln
            1235                1240                1245

Asn Gly Leu Lys Tyr Ile Ala Ile Asp Val Arg Glu Glu Pro Gly Leu
    1250                1255                1260

Pro Pro Gln Pro Gln Pro Pro Pro Leu Pro Gln Pro Gly Asp
1265                1270                1275                1280

Lys Ser Ser Trp Gly Arg Thr Arg Ser Leu Gly Gly Leu Ile Ser Ala
            1285                1290                1295

Val Gly Val Gly Ser Thr Arg Gly Gly Cys Gly Gly Pro Gly Pro Gly
        1300                1305                1310

Ala Pro Ala Pro Cys Pro Thr Thr Tyr Ala Gln His
        1315                1320

<210> SEQ ID NO 3
<211> LENGTH: 494
<212> TYPE: PRT
<213> ORGANISM: Rattus norvegicus

<400> SEQUENCE: 3

Met Lys Pro Ala Gly Thr Gly Pro Thr Val Ser Ser Gly Gly Glu Ser
1               5                   10                  15

Thr Asp Val Ser Leu Gly Pro Pro Phe Pro Trp Pro Cys Pro Pro Asp
                20                  25                  30

Val Arg Leu Cys Gly His Leu Arg Lys Gln Lys Ser Gln Arg Arg Arg
            35                  40                  45

Phe Phe Val Leu Arg Ala Asp Pro Pro Arg Leu Glu Cys Tyr Glu Ser
        50                  55                  60

Glu Lys Lys Phe Leu Ala Ser Gly Cys Arg Pro Pro Arg Pro Arg Arg
65                  70                  75                  80

Thr Val Ser Leu Glu Gly Ala Cys Thr Ile Ser Lys Arg Ala Asp Ala
                85                  90                  95
```

```
Arg Gln Arg His Leu Ile Val Ile Tyr Thr Ser Asp Ser Ser Leu Gly
                100                 105                 110

Val Ala Ala Ala Ser Glu Ala Glu Gln Gln Thr Trp Tyr Ser Ala Leu
            115                 120                 125

Leu Glu Val Arg Ala Thr Ala Ala Ala Ala Thr Ala Met Gly
130             135                 140

Phe Ser Pro Gln Glu Ala Pro Glu Ser Trp Ile Phe Ala Pro Phe Gln
145                 150                 155                 160

Asp Val Trp Pro Val Thr Leu Arg Ser Lys Gly Leu Gly Arg Ala Pro
                165                 170                 175

Gly Leu Ser Ser Gly Ser Tyr Arg Leu Cys Leu Gly Ser Gly Ala Leu
            180                 185                 190

Ser Leu Leu Arg Lys Pro Gly Ser Lys Gly Ser Arg Asp Ser Arg Ala
                195                 200                 205

Thr Pro Pro Pro Val Leu Arg Leu Ser Leu Leu Ser Val Arg Arg Cys
            210                 215                 220

Gly His Ala Asp Ser Phe Phe Phe Leu Glu Leu Gly Arg Ser Ala Pro
225                 230                 235                 240

Ile Gly Pro Gly Glu Leu Trp Leu Gln Ala Pro Asp Ala Val Val Ala
                245                 250                 255

Gln Ser Ile His Glu Thr Val Leu Ala Ala Met Lys Arg Leu Gly Ser
            260                 265                 270

Ser Ala Ala Ser Gly Lys Ala Glu Ala Pro Leu Gly Asp Ser Pro Lys
            275                 280                 285

Gly Ala Ser Ala Val Pro Ala Pro Ala Pro Tyr Glu Ile Pro Ala Leu
            290                 295                 300

Ala Leu Ala Ala Gln Ala Arg Ser Pro Gly Glu Arg Ala Lys Gln Asp
305                 310                 315                 320

Tyr Val Asn Pro Leu Glu Arg Met Gly Ser Ala Pro Ser Tyr Arg Gly
                325                 330                 335

Pro Asp Leu Gly Gly Asp Tyr Ile Ala Met Gly Met Arg Asn Asp Tyr
            340                 345                 350

Val His Met Gly Gly Lys Ala Ala Glu Tyr Met Trp Met Ala Pro Pro
            355                 360                 365

Gly Leu Pro Pro Thr Pro Pro Arg Val Asp Pro Arg Lys Glu Pro
            370                 375                 380

Glu Asp Cys Glu Ser Thr Glu Tyr Met Pro Met Asn Arg Phe Leu Pro
385                 390                 395                 400

Gly Pro Leu Tyr Tyr Glu Phe Lys Ala Arg Glu Pro Glu His Gly His
                405                 410                 415

Ser Ser Ala Gln Cys Ser Ile Arg Asp Arg Trp Arg Pro Met Val Ala
            420                 425                 430

Gln Pro Arg Ser Ser Gln Gly Ser Glu Leu Ser Gly Asp Tyr Met Tyr
            435                 440                 445

Ile Pro Asp Tyr Pro Ser Ala Arg Leu Gly Ser Leu Asp Ser Cys Leu
450                 455                 460

Asn Tyr Val Asp Leu Asp Leu Val Pro Pro Leu Glu Val Pro Gly Ala
465                 470                 475                 480

Ala Pro Gly Asn Ser Pro His Ser Tyr Ala Ser Ile Lys Phe
                485                 490

<210> SEQ ID NO 4
<211> LENGTH: 1257
```

<212> TYPE: PRT
<213> ORGANISM: Homo sapiens

<400> SEQUENCE: 4

```
Met Ala Ser Cys Ser Phe Thr Arg Asp Gln Ala Thr Arg Arg Leu Arg
 1               5                  10                  15

Gly Ala Ala Ala Ala Ala Ala Leu Ala Ala Val Val Thr Thr
             20                  25                  30

Pro Leu Leu Ser Ser Gly Thr Pro Thr Ala Leu Ile Gly Thr Gly Ser
         35                  40                  45

Ser Cys Pro Gly Ala Met Trp Leu Ser Thr Ala Thr Gly Ser Arg Ser
     50                  55                  60

Asp Ser Glu Ser Glu Glu Asp Leu Pro Val Gly Glu Val Cys
65                  70                  75                  80

Lys Arg Gly Tyr Leu Arg Lys Gln Lys His Gly His Arg Arg Tyr Phe
                 85                  90                  95

Val Leu Lys Leu Glu Thr Ala Asp Ala Pro Ala Arg Leu Glu Tyr Tyr
            100                 105                 110

Glu Asn Ala Arg Lys Phe Arg His Ser Val Arg Ala Ala Ala Ala Ala
        115                 120                 125

Ala Ala Ala Ala Ala Ser Gly Ala Ala Ile Pro Pro Leu Ile Pro Pro
    130                 135                 140

Arg Arg Val Ile Thr Leu Tyr Gln Cys Phe Ser Val Ser Gln Arg Ala
145                 150                 155                 160

Asp Ala Arg Tyr Arg His Leu Ile Ala Leu Phe Thr Gln Asp Glu Tyr
                165                 170                 175

Phe Ala Met Val Ala Glu Asn Glu Ser Glu Gln Glu Ser Trp Tyr Leu
            180                 185                 190

Leu Leu Ser Arg Leu Ile Leu Glu Ser Lys Arg Arg Arg Cys Gly Thr
        195                 200                 205

Leu Gly Ala Gln Pro Asp Gly Glu Pro Ala Ala Leu Ala Ala Ala Ala
    210                 215                 220

Ala Ala Glu Pro Pro Phe Tyr Lys Asp Val Trp Gln Val Ile Val Lys
225                 230                 235                 240

Pro Arg Gly Leu Gly His Arg Lys Glu Leu Ser Gly Val Phe Arg Leu
                245                 250                 255

Cys Leu Thr Asp Glu Glu Val Val Phe Val Arg Leu Asn Thr Glu Val
            260                 265                 270

Ala Ser Val Val Val Gln Leu Leu Ser Ile Arg Arg Cys Gly His Ser
        275                 280                 285

Glu Gln Tyr Phe Phe Leu Glu Val Gly Arg Ser Thr Val Ile Gly Pro
    290                 295                 300

Gly Glu Leu Trp Met Gln Val Asp Asp Cys Val Val Ala Gln Asn Met
305                 310                 315                 320

His Glu Leu Phe Leu Glu Lys Met Arg Ala Leu Cys Ala Asp Glu Tyr
                325                 330                 335

Arg Ala Arg Cys Arg Ser Tyr Ser Ile Ser Ile Gly Ala His Leu Leu
            340                 345                 350

Thr Leu Leu Ser Ala Arg Arg His Leu Gly Leu Val Pro Leu Glu Pro
        355                 360                 365

Gly Gly Trp Leu Arg Arg Ser Arg Phe Glu Gln Phe Cys His Leu Arg
    370                 375                 380

Ala Ile Gly Asp Gly Glu Asp Glu Met Leu Phe Thr Arg Phe Val
385                 390                 395                 400
```

-continued

```
Thr Pro Ser Glu Pro Val Ala His Ser Arg Arg Gly Arg Leu His Leu
            405                 410                 415
Pro Arg Gly Arg Arg Ser Arg Arg Ala Val Ser Val Pro Ala Ser Phe
        420                 425                 430
Phe Arg Arg Leu Ala Pro Ser Pro Ala Arg Pro Arg His Pro Ala Glu
    435                 440                 445
Ala Pro Asn Asn Gly Ala Arg Leu Ser Ser Glu Val Ser Gly Ser Gly
450                 455                 460
Ser Gly Asn Phe Gly Glu Gly Asn Pro Gln Gly Lys Glu Asp Gln
465                 470                 475                 480
Glu Gly Ser Gly Gly Asp Tyr Met Pro Met Asn Asn Trp Gly Ser Gly
                485                 490                 495
Asn Gly Arg Gly Ser Gly Gly Gln Gly Ser Asn Gly Gln Gly Ser
                500                 505                 510
Ser Ser His Ser Ser Gly Gly Asn Gln Cys Ser Gly Glu Gly Gln Gly
            515                 520                 525
Ser Arg Gly Gly Gln Gly Ser Asn Gly Gln Gly Ser Gly Gly Asn Gln
    530                 535                 540
Cys Ser Arg Asp Gly Gln Gly Thr Ala Gly Gly His Gly Ser Gly Gly
545                 550                 555                 560
Gly Gln Arg Pro Gly Gly His Gly Ser Gly Gly Gly Gln Gly Pro
                565                 570                 575
Gly Asp Gly His Gly Ser Gly Gly Gly Lys Asn Ser Gly Gly Gly Lys
                580                 585                 590
Gly Ser Gly Ser Gly Lys Gly Ser Asp Gly Asp Gly Glu Arg Gly Lys
            595                 600                 605
Ser Leu Lys Lys Arg Ser Tyr Phe Gly Lys Leu Thr Gln Ser Lys Gln
    610                 615                 620
Gln Gln Met Pro Pro Pro Pro Pro Pro Pro Pro Pro Pro Pro Pro Ala
625                 630                 635                 640
Gly Gly Thr Gly Gly Lys Gly Lys Ser Gly Gly Arg Phe Arg Leu Tyr
                645                 650                 655
Phe Cys Val Asp Arg Gly Ala Thr Lys Glu Cys Lys Glu Ala Lys Glu
                660                 665                 670
Val Lys Asp Ala Glu Ile Pro Glu Gly Ala Ala Arg Gly Pro His Arg
            675                 680                 685
Ala Arg Ala Phe Asp Glu Asp Glu Asp Pro Tyr Val Pro Met Arg
    690                 695                 700
Pro Gly Val Ala Thr Pro Leu Val Ser Ser Ser Asp Tyr Met Pro Met
705                 710                 715                 720
Ala Pro Gln Asn Val Ser Ala Ser Lys Lys Arg His Ser Arg Ser Pro
                725                 730                 735
Phe Glu Asp Ser Arg Gly Tyr Met Met Met Phe Pro Arg Val Ser Pro
                740                 745                 750
Pro Pro Ala Pro Ser Pro Pro Lys Ala Pro Asp Thr Asn Lys Glu Asp
            755                 760                 765
Asp Ser Lys Asp Asn Asp Ser Glu Ser Asp Tyr Met Phe Met Ala Pro
    770                 775                 780
Gly Ala Gly Ala Ile Pro Lys Asn Pro Arg Asn Pro Gln Gly Gly Ser
785                 790                 795                 800
Ser Ser Lys Ser Trp Ser Ser Tyr Phe Ser Leu Pro Asn Pro Phe Arg
                805                 810                 815
```

-continued

```
Ser Ser Pro Leu Gly Gln Asn Asp Asn Ser Glu Tyr Val Pro Met Leu
            820                 825                 830

Pro Gly Lys Phe Leu Gly Arg Gly Leu Asp Lys Glu Val Ser Tyr Asn
        835                 840                 845

Trp Asp Pro Lys Asp Ala Ala Ser Lys Pro Ser Gly Glu Gly Ser Phe
    850                 855                 860

Ser Lys Pro Gly Asp Gly Gly Ser Pro Ser Lys Pro Ser Asp His Glu
865                 870                 875                 880

Pro Pro Lys Asn Lys Ala Lys Arg Pro Asn Arg Leu Ser Phe Ile Thr
                885                 890                 895

Lys Gly Tyr Lys Ile Lys Pro Lys Pro Gln Lys Pro Thr His Glu Gln
            900                 905                 910

Arg Glu Ala Asp Ser Ser Ser Asp Tyr Val Asn Met Asp Phe Thr Lys
        915                 920                 925

Arg Glu Ser Asn Thr Pro Ala Pro Ser Thr Gln Gly Leu Pro Asp Ser
    930                 935                 940

Trp Gly Ile Ile Ala Glu Pro Arg Gln Ser Ala Phe Ser Asn Tyr Val
945                 950                 955                 960

Asn Val Glu Phe Gly Val Pro Phe Pro Asn Pro Ala Asn Asp Leu Ser
                965                 970                 975

Asp Leu Leu Arg Ala Ile Pro Arg Ala Asn Pro Leu Ser Leu Asp Ser
            980                 985                 990

Ala Arg Trp Pro Leu Pro Pro Leu Pro Leu Ser Ala Thr Gly Ser Asn
        995                 1000                1005

Ala Ile Glu Glu Glu Gly Asp Tyr Ile Glu Val Ile Phe Asn Ser Ala
    1010                1015                1020

Met Thr Pro Ala Met Ala Leu Ala Asp Ser Ala Ile Arg Tyr Asp Ala
1025                1030                1035                1040

Glu Thr Gly Arg Ile Tyr Val Val Asp Pro Phe Ser Glu Cys Cys Met
                1045                1050                1055

Asp Ile Ser Leu Ser Pro Ser Arg Cys Ser Glu Pro Pro Pro Val Ala
            1060                1065                1070

Arg Leu Leu Gln Glu Glu Glu Gln Arg Arg Pro Gln Ser Arg
        1075                1080                1085

Ser Gln Ser Phe Phe Ala Ala Ala Arg Ala Ala Val Ser Ala Phe Pro
    1090                1095                1100

Thr Asp Ser Leu Glu Arg Asp Leu Ser Pro Ser Ser Ala Pro Ala Val
1105                1110                1115                1120

Ala Ser Ala Ala Glu Pro Thr Leu Ala Leu Ser Gln Val Val Ala Ala
                1125                1130                1135

Ala Ser Ala Leu Ala Ala Ala Pro Gly Ile Gly Ala Ala Ala Ala Ala
            1140                1145                1150

Ala Gly Phe Asp Ser Ala Ser Ala Arg Trp Phe Gln Pro Val Ala Asn
        1155                1160                1165

Ala Ala Asp Ala Glu Ala Val Arg Gly Ala Gln Asp Val Ala Gly Gly
    1170                1175                1180

Ser Asn Pro Gly Ala His Asn Pro Ser Ala Asn Leu Ala Arg Gly Asp
1185                1190                1195                1200

Asn Gln Ala Gly Gly Ala Ala Ala Ala Ala Ala Pro Glu Pro Pro
                1205                1210                1215

Pro Arg Ser Arg Arg Val Pro Arg Pro Glu Arg Glu Asp Ser Asp
            1220                1225                1230

Asn Asp Asp Asp Thr His Val Arg Met Asp Phe Ala Arg Arg Asp Asn
```

Gln Phe Asp Ser Pro Lys Arg Gly Arg
    1250                1255

<210> SEQ ID NO 5
<211> LENGTH: 5828
<212> TYPE: DNA
<213> ORGANISM: Homo sapiens

<400> SEQUENCE: 5

| | | | | | | |
|---|---|---|---|---|---|---|
| cggcggcgcg | gtcggagggg | gccggcgcgc | agagccagac | gccgccgctt | gttttggttg | 60 |
| gggctctcgg | caactctccg | aggaggagga | ggaggaggga | ggagggagaga | agtaactgca | 120 |
| gcggcagcgc | cctcccgagg | aacaggcgtc | ttccccgaac | ccttcccaaa | cctcccccat | 180 |
| cccctctcgc | ccttgtcccc | tccctcctc | cccagccgcc | tggagcgagg | ggcagggatg | 240 |
| agtctgtccc | tccggccggt | ccccagctgc | agtggctgcc | cggtatcgtt | tcgcatggaa | 300 |
| aagccacttt | ctccacccgc | cgagatgggc | ccggatgggg | ctgcagagga | cgcgcccgcg | 360 |
| ggcggcggca | gcagcagcag | cagcagcagc | agcaacagca | acagccgcag | cgccgcggtc | 420 |
| tctgcgactg | agctggtatt | tgggcggctg | gtggcggctg | ggacggttgg | ggggtgggag | 480 |
| gaggcgaagg | aggagggaga | accccgtgca | acgttgggac | ttggcaaccc | gcctcccccct | 540 |
| gcccaaggat | atttaatttg | cctcgggaat | cgctgcttcc | agaggggaac | tcaggaggga | 600 |
| aggcgcgcgc | gcgcgcgcgc | tcctggaggg | gcaccgcagg | gaccccgac | tgtcgcctcc | 660 |
| ctgtgccgga | ctccagccgg | ggcgacgaga | gatgcatctt | cgctccttcc | tggtggcggc | 720 |
| ggcggctgag | aggagacttg | gctctcggag | gatcgggget | gccctcaccc | cggacgcact | 780 |
| gcctccccgc | cggcgtgaag | cgcccgaaaa | ctccggtcgg | gctctctcct | gggctcagca | 840 |
| gctgcgtcct | ccttcagctg | ccccctcccg | gcgcgggggg | cggcgtggat | ttcagagtcg | 900 |
| gggtttctgc | tgcctccagc | cctgtttgca | tgtgccgggc | gcgcggcgagg | agcctccgcc | 960 |
| ccccacccgg | ttgttttttcg | gagcctcct | ctgctcagcg | ttggtggtgg | cgtggcagc | 1020 |
| atggcgagcc | ctccggagag | cgatggcttc | tcggacgtgc | gcaaggtggg | ctacctgcgc | 1080 |
| aaacccaaga | gcatgcacaa | acgcttcttc | gtactgcgcg | cggccagcga | ggctgggggc | 1140 |
| ccggcgcgcg | tcgagtacta | cgagaacgag | aagaagtggc | ggcacaagtc | gagcgccccc | 1200 |
| aaacgctcga | tcccccttga | gagctgcttc | aacatcaaca | gcgggctgga | ctccaagaac | 1260 |
| aagcacctgg | tggctctcta | cacccgggac | gagcactttg | ccatcgcggc | ggacagcgag | 1320 |
| gccgagcaag | acagctggta | ccaggctctc | ctacagctgc | acaaccgtgc | taagggccac | 1380 |
| cacgacggag | ctgcggcct | cggggcggga | ggtggtgggg | gcagctgcag | cggcagctcc | 1440 |
| ggccttggtg | aggctgggga | ggacttgagc | tacggtgacg | tgccccagg | accgcattc | 1500 |
| aaagaggtct | ggcaagtgat | cctgaagccc | aagggcctgg | gtcagacaaa | gaacctgatt | 1560 |
| ggtatctacc | gcctttgcct | gaccagcaag | accatcagct | tcgtgaagct | gaactcggag | 1620 |
| gcagcggccg | tggtgctgca | gctgatgaac | atcaggcgct | gtggccactc | ggaaaacttc | 1680 |
| ttcttcatcg | aggtgggccg | ttctgccgtg | acggggcccg | gggagttctg | gatgcaggtg | 1740 |
| gatgactctg | tggtggccca | gaacatgcac | gagaccatcc | tggaggccat | gcgggccatg | 1800 |
| agtgatgagt | tccgccctcg | cagcaagagc | cagtcctcgt | ccaactgctc | taaccccatc | 1860 |
| agcgtccccc | tgcgcggca | ccatctcaac | aatcccccgc | ccagccaggt | ggggctgacc | 1920 |
| cgccgatcac | gcactgagag | catcaccgcc | acctcccccgg | ccagcatggt | gggcgggaag | 1980 |

```
ccaggctcct tccgtgtccg cgcctccagt gacggcgaag gcaccatgtc ccgcccagcc   2040
tcggtggacg gcagccctgt gagtcccagc accaacagaa cccacgccca ccggcatcgg   2100
ggcagcgccc ggctgcaccc cccgctcaac cacagccgct ccatccccat gccggcttcc   2160
cgctgctcgc cttcggccac cagcccggtc agtctgtcgt ccagtagcac cagtggccat   2220
ggctccacct cggattgtct cttcccacgg cgatctagtg cttcggtgtc tggttccccc   2280
agcgatggcg gtttcatctc ctcggatgag tatggctcca gtccctgcga tttccggagt   2340
tccttccgca gtgtcactcc ggattccctg gccacaccc caccagcccg cggtgaggag   2400
gagctaagca actatatctg catgggtggc aaggggccct ccaccctgac cgcccccaac   2460
ggtcactaca ttttgtctcg gggtggcaat ggccaccgct gcaccccagg aacaggcttg   2520
ggcacgagtc cagccttggc tggggatgaa gcagccagtg ctgcagatct ggataatcgg   2580
ttccgaaaga gaactcactc ggcaggcaca tcccctacca ttacccacca gaagaccccg   2640
tcccagtcct cagtggcttc cattgaggag tacacagaga tgatgcctgc ctacccacca   2700
ggaggtggca gtggaggccg actgccggga cacaggcact ccgccttcgt gcccacccgc   2760
tcctacccag aggagggtct ggaaatgcac cccttggagc gtcgggggggg gcaccaccgc   2820 ccagacagct ccaccctcca cacggatgat ggctacatgc ccatgtcccc aggggtggcc   2880
ccagtgccca gtggccgaaa gggcagtgga gactatatgc ccatgagccc caagagcgta   2940
tctgccccac agcagatcat caatcccatc agacgccatc cccagagagt ggaccccaat   3000
ggctacatga tgatgtcccc cagcggtggc tgctctcctg acattggagg tggccccagc   3060
agcagcagca gcagcagcaa cgccgtccct tccgggacca gctatggaaa gctgtggaca   3120
aacggggtag ggggccacca ctctcatgtc ttgcctcacc ccaaaccccc agtggagagc   3180
agcggtggta agctcttacc ttgcacaggt gactacatga acatgtcacc agtggggggac   3240 tccaacacca gcagccctc cgactgctac tacggccctg aggacccca gcacaagcca   3300 gtcctctcct actactcatt gccaagatcc tttaagcaca cccagcgccc cggggagccg   3360
gaggagggtg cccggcatca gcacctccgc ctttccacta gctctggtcg ccttctctat   3420
gctgcaacag cagatgattc ttcctcttcc accagcagcg acagcctggg tgggggatac   3480
tgcggggcta ggctggagcc cagccttcca catccccacc atcaggttct gcagccccat   3540
ctgcctcgaa aggtggacac agctgctcag accaatagcc gcctggcccg gcccacgagg   3600
ctgtccctgg gggatcccaa ggccagcacc ttacctcggg cccgagagca gcagcagcag   3660
cagcagccct tgctgcaccc tccagagccc aagagcccgg gggaatatgt caatattgaa   3720
tttgggagtg atcagtctgg ctacttgtct ggcccggtgg cttttccacag ctcaccttct   3780 gtcaggtgtc catcccagct ccagccagct cccagagagg aagagactgg cactgaggag   3840
tacatgaaga tggacctggg gccgggccgg agggcagcct ggcaggagag cactgggtc    3900 gagatgggca gactgggccc tgcacctccc ggggctgcta gcatttgcag gcctacccgg   3960
gcagtgccca gcagccgggg tgactacatg accatgcaga tgagttgtcc ccgtcagagc   4020
tacgtggaca cctcgccagc tgcccctgta agctatgctg acatgcgaac aggcattgct   4080
gcagaggagg tgagcctgcc cagggccacc atggctgctg cctcctcatc ctcagcagcc   4140
tctgcttccc cgactgggcc tcaagggca gcagagctgg ctgccactc gtccctgctg   4200 gggggcccac aaggacctgg gggcatgagc gccttcaccc gggtgaacct cagtcctaac   4260
cgcaaccaga gtgccaaagt gatccgtgca gaccacaag ggtgccggcg gaggcatagc   4320
tccgagactt tctcctcaac acccagtgcc acccgggtgg gcaacacagt gcccttggga   4380
```

```
gcggggcag cagtaggggg cggtggcggt agcagcagca gcagcgagga tgtgaaacgc    4440
cacagctctg cttcctttga gaatgtgtgg ctgaggcctg gggagcttgg gggagccccc    4500
aaggagccac ccaaactgtg tggggctgct ggggtttgg agaatggtct taactacata    4560
gacctggatt tggtcaagga cttcaaacag tgccctcagg agtgcacccc tgaaccgcag    4620
cctcccccac ccccaccccc tcatcaaccc ctgggcagcg gtgagagcag ctccacccgc    4680
cgctcaagtg aggatttaag cgcctatgcc agcatcagtt ccagaagca gccagaggac    4740 cgtcagtagc tcaactggac atcacagcag aatgaagacc taaatgacct cagcaaatcc    4800
tcttctaact catgggtacc cagactctaa atatttcatg attcacaact aggacctcat    4860
atcttcctca tcagtagatg gtacgatgca tccatttcag tttgtttact ttatccaatc    4920
ctcaggattt cattgactga actgcacgtt ctatattgtg ccaagcgaaa aaaaaaaatg    4980
cactgtgaca ccagaataat gagtctgcat aaacttcatc ttcaacctta aggacttagc    5040
tggccacagt gagctgatgt gcccaccacc gtgtcatgag agaatgggtt tactctcaat    5100
gcattttcaa gatacatttc atctgctgct gaaactgtgt acgacaaagc atcattgtaa    5160
attatttcat acaaaactgt tcacgttggg tggagagagt attaaatatt taacataggt    5220
tttgatttat atgtgtaatt ttttaaatga aaatgtaact tttcttacag cacatctttt    5280
ttttggatgt gggatggagg tatacaatgt tctgttgtaa agagtggagc aaatgcttaa    5340
aacaaggctt aaaagagtag aatagggtat gatccttgtt ttaagattgt aattcagaaa    5400
acataatata agaatcatag tgccatagat ggttctcaat tgtatagtta tatttgctga    5460
tactatctct tgtcatataa acctgatgtt gagctgagtt ccttataaga attaatctta    5520
attttgtatt ttttcctgta agacaatagg ccatgttaat taaactgaag aaggatatat    5580
ttggctgggt gttttcaaat gtcagcttaa aattggtaat tgaatggaag caaaattata    5640
agaagaggaa attaaagtct tccattgcat gtattgtaaa cagaaggaga tgggtgattc    5700
cttcaattca aaagctctct ttggaatgaa caatgtgggc gtttgtaaat tctggaaatg    5760
tctttctatt cataataaac tagatactgt tgatctttta aaaaaaaaaa aaaaaaaaa    5820 aaaaaaaa                                                              5828
```

<210> SEQ ID NO 6
<211> LENGTH: 3975
<212> TYPE: DNA
<213> ORGANISM: Homo sapiens

<400> SEQUENCE: 6

```
atggcgagcc cgccgcggca cgggccgccc gggccggcga gcggagacgg ccccaacctc     60
aacaacaaca acaacaacaa caaccacagc gtgcgcaagt gcggctacct gcgcaagcag    120
aagcatggcc acaagcgctt cttcgtgctg cgcggacccg gcgcgggcgg cgacaaggcc    180
acggcgggcg gggggtcggc gccgcaaccg ccgcggctcg agtactacga aagcgaaaaa    240
aattggcgga gcaaggcagg cgcgccgaaa cgggtgatcg ctctcgactg ctgcctgaac    300
atcaacaagc gcgccgaccc caagcacaag tacctgatcg ccctctacac caaggacgag    360
tacttcgccg tggccgccga gaacgagcag gagcaggagg gctggtaccg cgcgctcacc    420
gacctggtca gcgagggccg gcggccgccc ggagacgcgc ccccgccgc cgcgcccgcc    480 gcgtcctgca gcgcctccct gcccggcgcc gtgggcggtt ctgccggcgc cgccggggcc    540
gaggacagct acgggctggt ggctcccgcc acggccgcc accgtgaggt gtggcaggtg    600
```

```
aacctgaagc ccaagggtct gggccagagc aagaacctga cggggggtgta ccgtctgtgc    660
ctgtctgcgc gcaccatcgg cttcgtgaag ctcaactgcg agcagccgtc ggtgacgctg    720
cagctcatga acatccgccg ctgcggccac tcggacagct tcttcttcat cgaggtgggc    780
cgctcggccg tcacaggccc cggcgagctg tggatgcagg cggacgactc ggtggtggcg    840
cagaacatcc acgagaccat cctggaggcc atgaaggcgc tcaaggagct cttcgagttc    900
cggccgcgca gtaagagcca atcgtcgggg tcgtcggcca cgcacccccat cagcgtcccc    960
ggcgcgcgcc gccaccacca cctggtcaac ctgcccccca gccagacggg cctggtgcgc   1020
cgctcgcgca ccgacagcct ggccgccacc ccgccggcgg ccaagtgcag ctcgtgccgg   1080
gtgcgcaccg ccagcgaggg cgacggcggc gcggcggcgg agcggcggc cgcgggcgcc   1140
aggccggtgt cggtggctgg gagccccctg agccccgggc cggtgcgcgc gcccctgagc   1200
cgctcgcaca ccctgatcgg cggctgccgg gccgcgggaa caaagtggca ttgcttcccg   1260
gcagggggcg gattgcaaca cagccgttcg atgtccatgc ccgtggagca tttgccgcca   1320
gccgccacca gcccgggttc cttgtcttcc agcagcgacc acggttgggg ttcttacccg   1380
ccgccgcccg gcccgcaccc gcttttgccg catccgttgc accacggccc cggccagcgg   1440
ccttccagcg gcagcgcttc cgcttcgggc tcccccagcg accccggttt catgtccctg   1500
gacgagtacg gctccagccc aggcgacctg cgcgccttct gcagccaccg aagcaacacg   1560
cccgagtcca tcgcggagac gccccccggcc cgagacggcg gcggcggcgg tgagttttac   1620
gggtacatga ccatggacag gcccctgagc cactgtggcc gctcctaccg ccgggtctcg   1680
ggggacgcgg cccaggacct ggaccgaggg ctgcgcaaga ggacctactc cctgaccacg   1740
ccagcccggc agcggccggt gccccagccc tcctctgcct cgctggatga atacacccctg   1800
atgcgggcca ccttctcggg cagcgcgggc cgcctctgcc cgtcctgccc cgcgtcctct   1860
cccaaggtgg cctaccaccc ctacccagag gactacggag acatcgagat cggctcccac   1920
aggagctcca gcagcaacct gggggcagac gacggctaca tgcccatgac gcccggcgcg   1980
gcccttgcgg gcagtgggag cggcagctgc aggagcgacg actacatgcc catgagcccc   2040
gccagcgtgt ccgcccccaa gcagattttg cagcccaggg ccgccgccgc cgccgccgcc   2100
gccgtgcctt ttgcggggcc tgcggggcca gcaccccact ttgcggcggg caggacattc   2160
ccggcgagtg ggggcggcta caaggccagc tcgcccgccg agagctcccc cgaggacagt   2220
gggtacatgc gcatgtggtg cggttccaag ctgtccatgg agcatgcaga tggcaagctg   2280
ctgcccaacg gggactacct caacgtgtcc cccagcgacg cggtcaccac gggcacccgg   2340
cccgacttct tctccgcagc cctgcacccc ggcggggagc cgctcagggg cgttcccggc   2400
tgctgctaca gctccttgcc ccgctcctac aaggccccct acaacctgtgg cggggacagc   2460
gaccagtacg tgctcatgag ctcccccgtg gggcgcatcc tggaggagga gcgtctggag   2520
cctcaggcca cccagggcc cacccaggcg gccagcgcct cggggccggg ccccacgcag   2580
cccccctcacc ctgtagtgcc ttcgcccgtg cggcctagcg gcggccgccc ggagggcttc   2640
ttgggccagc gcgccgggc ggtgaggccc acgcgcctgt ccctggaggg gctgccagcc   2700
ctgcccagca tgcacgagta cccactgcca ccggagccca gagccccgg cgagtacatc   2760
aacatcgact ttggcgagcc cggggcccgc tgtcgccgc ccgcgcctcc cctgctggcg   2820
tcggcggcct cgtcctcatc gctattgtcc gccagcagcc ggccttgtc gttgggctca   2880
ggcaccccgg gcaccagcag cgacagccgg cagcggtctc cgctctccga ctacatgaac   2940
ctcgacttca gctcccccaa gtctcctaag ccgggcgccc cgagcggcca cccgtgggc   3000
```

```
tccttggacg gcctcctgtc ccccgaggcc tcctccccgt atccgccgtt gccccgcgt      3060 ccgtccgcgt cccgtcgtc gtctctgcag ccgccgccac cgccgccggc cccggggag      3120 ctgtaccgcc tgcccccgc ctcggccgtt gccaccgccc agggcccggg cgccgcctca      3180
tcgttgtcct cggacaccgg ggacaatggt gactacaccg agatggcttt tggtgtggcc      3240
gccaccccgc cgcaacctat cgcggccccc ccgaagccag aagctgcccg cgtggccagc      3300
ccgacgtcgg gcgtgaagag gctgagcctc atggagcagg tgtcgggagt cgaggccttc      3360
ctgcaggcca gccagccccc ggaccccac cgcggcgcca aggtcatccg cgcagacccg      3420
caggggggcc gccgccgcca cagttccgag accttctcct ccaccacgac ggtcaccccc      3480
gtgtccccgt ccttcgccca aaccccaag cgccacaact cggcctccgt ggaaaatgtc      3540
tctctcagga aaagcagcga gggcggcgtg gtgtcggcc ctggagggg cgacgagccg      3600 cccacctccc cacgacagtt gcagccgcg ccccctttgg caccgcaggg ccggccgtgg      3660
accccgggtc agcccggggg cttggtcggt tgtcctggga gcggtggatc gcccatgcgc      3720
agagagacct ctgccggttt ccagaatggt ctcaagtaca tcgccatcga cgtgagggag      3780
gagcccgggc tgccacccca gccgcagccg ccgccgccgc cgcttcctca gccgggagac      3840
aagagctcct ggggcggac ccgaagcctc gggggtctca tcagcgctgt gggcgtcggc      3900
agcacccgcg gcgggtgcgg ggggccgggt cccggtgccc ctgcccctg cccaacaacc      3960 tacgcccagc attga                                                    3975

<210> SEQ ID NO 7
<211> LENGTH: 1969
<212> TYPE: DNA
<213> ORGANISM: Rattus norvegicus

<400> SEQUENCE: 7
gggacacacg caccctgtac aggctccttg cccactccaa gtcaggagag ggcgtggaga        60
gatgcagggc agctaggccg gttgcaatct tcccaagatt gcaacttgtc ccaagccggt       120
ggtagctcag gggacaggac ccattcaaat tagtccttct gaggacagtt tactgccttt       180
ggctggagat gaagcctgca ggtacgggcc ccacagtctc ctctgggggc gagtccaccg       240
acgtgtccct cggcccgccg tttccttggc cctgccgcc cgacgtgcgg ctctgtggcc       300
atctgaggaa gcagaagtcc cagcgccgcc gcttttttcgt gcttgcgtgct gacccaccac       360 ggctggagtg ctatgagagc gagaagaagt tcttggccag cggctgccgc ccacctcgac       420
cccggcgtac cgttagcctg aaggtgcct gcactattag caagcgcgcg gatgcccgtc       480
agcgccacct gatcgtcatc tataccgcg acagcagcct gggcgtggcg gcggccagtg       540
aagcagagca gcaaacatgg tacagcgcct tgctcgaggt gcgcgccacc gccgctgcag       600
ctgctgccac cgctatgggt ttcagccccc aagaggcccc tgagtcttgg atcttcgccc       660
cgttccagga cgtctggcct gtgacactgc ggtccaaggg gctggggaga gcaccaggcc       720
tgagcagcgg cagctatcgc ctgtgcctgg gttctgggc cctgagcctc ctgcggaagc       780
cgggaagcaa aggctccaga gacagccggg caacgccacc accagtcctg cgcttgtcct       840
tgcttagtgt gcgccgctgc ggccacgcag attcctttt cttcctggaa ctcgggcgct       900
cagcgcccat aggtcctggt gagctgtggc tgcaggcccc tgatgcagtg gtggcccaaa       960
gcattcatga ccgtcctg gctgccatga agagactggg gagcagtgca gccagtggca      1020
aagctgaggc accgctggga gattctccaa aggggggctt tgcagtccct gccccagcac      1080
```

-continued

| | |
|---|---|
| catatgagat ccctgctttg gcactggcag cacaagcgag aagtccgggt gagagagcga | 1140 |
| agcaggacta cgtcaatcca ctggaaagga tggggtcagc accctcctac aggggggccag | 1200 |
| atctgggtgg ggactacatc gccatgggaa tgaggaatga ctatgtgcac atggggggga | 1260 |
| aagctgctga gtacatgtgg atggcgcccc caggtctccc tccccccacc cctcccaggg | 1320 |
| tagatcccag aaaggagcct gaggattgtg agagcacaga gtatatgccc atgaacagat | 1380 |
| ttttaccggg gcctctttac tacgagttca aggccaggga gcctgaacat gggcattcta | 1440 |
| gtgcccagtg tagcattagg gacagatgga gacccatggt ggctcagccc cgctcttccc | 1500 |
| aagggtcaga gctctctggg gactacatgt acatccctga ctatcccagt gctaggctgg | 1560 |
| ggtctctgga cagctgcctc aactatgtgg acctggacct agtccctccc ctggaggttc | 1620 |
| ctggagcggc cccagggaat agtccacata gctatgccag catcaagttc tagaactttc | 1680 |
| agaagatagg ggaggagaac caagcattgg ttagggaaga gaggaaaaga agagaaaacc | 1740 |
| ttagcactgt tcagctcagc ttctgcacat aggagccagg gactctgagg ccttgtgagg | 1800 |
| tgctatgctg ccccccttgcc tgctctgtct cttccagctg taccgcctca gaaacacctc | 1860 |
| aggaagaagt gctccaaaga aattagactc ttaagagaaa gtactagaac atctctctgc | 1920 |
| accccacccc caaacccaaa caacaaacaa ataaaacacc tacagaacc | 1969 |

<210> SEQ ID NO 8
<211> LENGTH: 3939
<212> TYPE: DNA
<213> ORGANISM: Homo sapiens

<400> SEQUENCE: 8

| | |
|---|---|
| ggtcagggta gttccccaac cctcccttc gtgaattccc cctcgtcctc gctcaccttta | 60 |
| aaaccatcgt gcatcaccat ggcgagttgc tccttcactc gcgaccaagc gacaagaaga | 120 |
| ctaagaggtg cagcagcggc ggcagcggca gctctagcag cagtggtgac caccccgctt | 180 |
| ctttcctcgg gaacccccgac cgcactcatt gggaccgggt cgtcttgtcc gggagccatg | 240 |
| tggctctcca cggccactgg ctccggtca gactccgagt ccgaaggagga ggacctgccc | 300 |
| gtcggggagg aagtctgcaa acgcggctac ctgcggaaac agaagcatgg gcacaggcgc | 360 |
| tacttcgtgc tcaaactcga gactgctgac gccccagctc ggctggaata ctacgaaaat | 420 |
| gccaggaagt tccggcacag tgtccgcgcc gcggcggctg cagcagcggc ggccgcctct | 480 |
| ggcgccgcga tcccccgct cattccaccg cggcgcgtga tcaccctata ccagtgcttt | 540 |
| tccgtgagcc agcgagcaga tgcaaggtac cgacacctca ttgctctttt cacccaagac | 600 |
| gaatacttcg cgatggtggc cgagaacgag tcggagcagg aaagctggta cttgctgctc | 660 |
| agccgcctca tcctcgagag caagcgccgc cgctgcggca cgctcggcgc gcagccggac | 720 |
| ggagagccgg ccgcgctggc ggcgcagcg gcggcggagc cacccttcta taaagatgtg | 780 |
| tggcaggtaa tagtcaaacc caggggggctg ggcacagaa aagagctgag cggcgtgttc | 840 |
| cggctgtgtc taaccgacga ggaggtcgtg tttgtgaggc tgaacaccga agtggccagc | 900 |
| gtggtcgtcc agctcctgag catccgtcgc tgtggacact cggagcagta tttcttcttg | 960 |
| gaagtaggca ggtccactgt catcggtccg ggagagctct ggatgcaggt cgatgactgt | 1020 |
| gtggttgccc aaaacatgca tgagctgttt ttggagaaga tgagagcctt gtgtgcagac | 1080 |
| gaatacagag cccgctgccg cagctacagc atcagcatcg gcgcccacct gttaacctg | 1140 |
| ctgtccgcta ggaggcacct gggcttggtg ccgctcgagc cggaggctg gctcagaagg | 1200 |
| tcccgctttg agcagttttg ccacctcagg gccatcggcg acggggaaga cgagatgctt | 1260 |

```
ttcaccaggc gcttcgtaac acccagcgag cctgtggccc actccaggcg aggaagactg    1320
cacctgccca gagggcgcag gtcaaggaga gcggtttcag tgccggccag cttttttcgc    1380
cgcttagcac ccagcccagc acgtccccgg caccctgcag aagccccgaa caatggagct    1440
cgcctgtctt ctgaagtgtc tggttctggc tctggcaact ttggggagga aggcaatccc    1500
cagggcaaag aagatcagga aggaagcgga ggtgactaca tgcctatgaa caattggggc    1560
tcaggaaatg gccggggctc aggaggtggc cagggctcaa atggccaagg ctccagtagc    1620
catagctcgg gaggaaacca gtgttcaggc gagggacagg gatcccgagg tggtcagggc    1680
tcaaatggcc agggctcagg aggaaaccag tgctctagag atggccaggg caccgcaggt    1740
gggcacggtt caggtggtgg ccagagacct ggaggtgggc atggctcagg tggtggccag    1800
ggacctggag atggccatgg ctcaggtggt ggcaagaact ctgggggggg caaaggctca    1860
ggaagtggga aaggatccga tggtgatggt gaacgtggaa atctctgaa gaaaagatcc    1920 tattttggca aattaactca aagcaagcaa cagcaaatgc caccacctcc accacctcct    1980
cctccacccc caccagctgg aggaactggt ggaaaaggga gtctggggg aagattcaga    2040 ctttattttt gtgttgacag aggagccacg aaagaatgca aagaagccaa agaagtgaaa    2100
gatgcagaga tcccagaagg tgcagctcga ggtccccaca gagccagagc ttttgatgaa    2160
gatgaggatg acccatacgt gccaatgagg ccaggggtgg ccaccccctct tgtaagctcc    2220 agtgattata tgccaatggc tcctcaaaat gtctctgctt caaaaaagcg ccactctcga    2280 tcccctttg aagattcaag agggtacatg atgatgtttc ccagagtgag cccaccacct    2340
gctccgagtc ctccaaaagc acctgatact aataaagagg atgactcaaa ggacaatgac    2400
agtgagagtg actacatgtt tatggctcct ggagccggtg caattccaaa aaaccccaga    2460
aatcctcagg gtggctcttc ctccaaaagt tggagctcct acttctctct accaaaccct    2520
tttcggagct cacctttggg acagaatgac aacagtgagt atgtgccaat gttacctgga    2580
aagttcctgg ggaggggcct agacaaagaa gtctcctata actgggaccc caaagatgca    2640
gcttcaaagc cttcaggtga gggatcattc tcaaagcctg gagatggggg atcaccttca    2700
aagccttcag atcatgagcc cccaaagaat aaagctaaga gacctaaccg acttttctttt    2760 attacaaaag gatataaaat caagccaaaa ccacaaaagc ccacacatga gcagagagaa    2820
gctgacagct ctagtgacta cgtcaacatg gacttcacta aaagagagag caatacacca    2880
gctccctcta ctcaaggact accagattcg tggggcataa ttgctgaacc cagacagtca    2940
gccttttcta attatgtgaa tgttgagttt ggagtgccat ttccaaatcc agcaaacgac    3000
ctctcagatc ttttaagagc tataccacgt gccaaccccct tatctctgga cagtgctagg    3060
tggccacttc ctcccttcc cctcagtgct acaggtagca atgctattga ggaagagggt    3120
gactacattg aagtaatttt caactcagca atgacaccag ccatggctct tgctgacagt    3180
gccattcgct atgatgctga aacaggtcga atctatgtgg tcgacccatt ttctgagtgc    3240
tgtatggata tttctctctc ccccagccga tgttctgaac caccacctgt agctaggctg    3300
ctgcaggaag aagagcagga gagaagacgc ccacaaagcc gttctcaaag tttcttttgca    3360 gcagccagag ccgctgtctc tgcttttcca acagacagcc tcgagagaga cctttccccca    3420 tcctcagccc cggctgtcgc ttcggctgca gagccgactt tagccctcag ccaagttgta    3480
gctgcggcct ccgcgctcgc cgcagccccg ggcatcggcg cagcagccgc agctgctgga    3540
tttgactccg cctctgcccg ctggtttcaa cctgttgcta atgctgctga tgccgaagca    3600
```

```
gtaagggag cccaagacgt tgccggtggc tcgaaccctg gagcccacaa cccatctgca    3660
aaccttgcca gaggtgataa ccaggctggc ggggctgccg ctgcagctgc cgctccggaa    3720
ccaccacctc gcagtcgccg ggtgccaaga ccccggaga gagaagattc tgacaacgac    3780
gacgacactc acgtgagaat ggattttgcc agacgtgata atcagttcga ctctcccaaa    3840
agaggtcggt aattttagaa ttaatttccc taaagtgaat ggtcattgtc taatgattcg    3900
atgcgctaca gtctacagtg ttagggtata tttcattaa                          3939
```

<210> SEQ ID NO 9
<211> LENGTH: 262
<212> TYPE: PRT
<213> ORGANISM: Homo sapiens

<400> SEQUENCE: 9

```
Asp Leu Asp Asn Arg Phe Arg Lys Arg Thr His Ser Ala Gly Thr Ser
 1               5                  10                  15

Pro Thr Ile Thr His Gln Lys Thr Pro Ser Gln Ser Ser Val Ala Ser
            20                  25                  30

Ile Glu Glu Tyr Thr Glu Met Met Pro Ala Tyr Pro Pro Gly Gly Gly
        35                  40                  45

Ser Gly Gly Arg Leu Pro Gly His Arg His Ser Ala Phe Val Pro Thr
    50                  55                  60

Arg Ser Tyr Pro Glu Glu Gly Leu Glu Met His Pro Leu Glu Arg Arg
65                  70                  75                  80

Gly Gly His His Arg Pro Asp Ser Ser Thr Leu His Thr Asp Asp Gly
                85                  90                  95

Tyr Met Pro Met Ser Pro Gly Val Ala Pro Val Pro Ser Gly Arg Lys
            100                 105                 110

Gly Ser Gly Asp Tyr Met Pro Met Ser Pro Lys Ser Val Ser Ala Pro
        115                 120                 125

Gln Gln Ile Ile Asn Pro Ile Arg Arg His Pro Gln Arg Val Asp Pro
    130                 135                 140

Asn Gly Tyr Met Met Met Ser Pro Ser Gly Gly Cys Ser Pro Asp Ile
145                 150                 155                 160

Gly Gly Gly Pro Ser Ser Ser Ser Ser Asn Ala Val Pro Ser
                165                 170                 175

Gly Thr Ser Tyr Gly Lys Leu Trp Thr Asn Gly Val Gly Gly His His
            180                 185                 190

Ser His Val Leu Pro His Pro Lys Pro Pro Val Glu Ser Ser Gly Gly
        195                 200                 205

Lys Leu Leu Pro Cys Thr Gly Asp Tyr Met Asn Met Ser Pro Val Gly
    210                 215                 220

Asp Ser Asn Thr Ser Ser Pro Ser Asp Cys Tyr Tyr Gly Pro Glu Asp
225                 230                 235                 240

Pro Gln His Lys Pro Val Leu Ser Tyr Tyr Ser Leu Pro Arg Ser Phe
                245                 250                 255

Lys His Thr Gln Arg Pro
            260
```